US009700605B2

(12) United States Patent
Ballou, Jr. et al.

(10) Patent No.: US 9,700,605 B2
(45) Date of Patent: Jul. 11, 2017

(54) VACCINE COMPRISING AN OIL IN WATER EMULSION

(71) Applicant: GlaxoSmithKline Biologicals S.A., Rixensart (BE)

(72) Inventors: William Ripley Ballou, Jr., Rixensart (BE); Emmanuel Jules Hanon, Rixensart (BE)

(73) Assignee: GlaxoSmithKline Biologicals S.A. (BE)

( * ) Notice: Subject to any disclaimer, the term of this patent is extended or adjusted under 35 U.S.C. 154(b) by 0 days.

(21) Appl. No.: 14/593,911

(22) Filed: Jan. 9, 2015

(65) Prior Publication Data

US 2015/0359863 A1 Dec. 17, 2015

Related U.S. Application Data

(62) Division of application No. 12/445,090, filed as application No. PCT/EP2007/060743, filed as application No. PCT/EP2006/069979 on Dec. 20, 2006, now abandoned.

(30) Foreign Application Priority Data

| Oct. 12, 2006 | (GB) | 0620336.8 |
| Oct. 12, 2006 | (GB) | 0620337.6 |
| Oct. 19, 2006 | (GB) | 0620815.1 |
| Oct. 19, 2006 | (GB) | 0620816.9 |
| Apr. 20, 2007 | (GB) | 0707697.9 |
| Jun. 12, 2007 | (GB) | 0711357 |
| Jun. 21, 2007 | (GB) | 0712062.9 |

(51) Int. Cl.
*A61K 39/00* (2006.01)
*A61K 39/12* (2006.01)
*A61K 39/145* (2006.01)
*A61K 39/39* (2006.01)

(52) U.S. Cl.
CPC ............. *A61K 39/00* (2013.01); *A61K 39/12* (2013.01); *A61K 39/145* (2013.01); *A61K 39/39* (2013.01); *A61K 2039/5252* (2013.01); *A61K 2039/55566* (2013.01); *A61K 2039/70* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| 4,235,877 A | 11/1980 | Fullerton et al. |
| 4,454,119 A | 6/1984 | Fukushi et al. |
| 4,652,518 A | 3/1987 | Makela et al. |
| 5,278,302 A | 1/1994 | Caruthers et al. |
| 5,666,153 A | 9/1997 | Copeland et al. |
| 2003/0133944 A1 | 7/2003 | Cohen et al. |
| 2009/0136543 A1 | 5/2009 | Ballou et al. |
| 2010/0189741 A1 | 7/2010 | Ballou et al. |

FOREIGN PATENT DOCUMENTS

| EP | 198474 | 10/1986 |
| EP | A0304578 | 3/1989 |
| EP | 366412 | 10/1989 |
| EP | 0362278 | 4/1990 |
| EP | A414374 | 2/1991 |
| EP | 468520 | 7/1991 |
| EP | 399843 | 7/1994 |
| EP | 1092444 | 4/2001 |
| WO | 90/01496 | 2/1990 |
| WO | 93/10152 | 5/1993 |
| WO | 94/21292 | 9/1994 |
| WO | 95/17210 | 6/1995 |
| WO | 95/26204 | 10/1995 |
| WO | 96/26277 | 8/1996 |
| WO | 96/33739 | 10/1996 |
| WO | 98/50567 | 11/1998 |
| WO | 99/11241 | 3/1999 |
| WO | 99/12565 | 3/1999 |
| WO | 99/17741 | 4/1999 |
| WO | 99/34850 | 7/1999 |
| WO | 01/22992 | 4/2001 |
| WO | 03/043572 | 5/2003 |
| WO | 2006/100110 | 9/2006 |
| WO | 2007/052155 | 10/2007 |
| WO | 2008/043774 | 4/2008 |

OTHER PUBLICATIONS

Jackson et al., Effect of Varying Doses of a Monovalent H7N9 Influenza Vaccine With and Without AS03 and MF59 Adjuvants on Immune Response A Randomized Clinical Trial, 2015, JAMA, vol. 314, No. 3, pp. 237-246.*
Sanofi Pasteur seasonal influenza package insert, Fluzone 2009-2010 seasonal influenza package insert, 2009.*

(Continued)

*Primary Examiner* — Benjamin P Blumel
(74) *Attorney, Agent, or Firm* — Joseph J. Schuller

(57) ABSTRACT

The present invention provides an immunogenic composition comprising an antigen or antigen composition and an adjuvant composition comprising an oil in water emulsion, wherein said oil in water emulsion comprises 0.5-10 mg metabolizable oil, 0.5-11 mg tocol and 0.1-4 mg emulsifying agent, per human dose.

5 Claims, 13 Drawing Sheets

(56) References Cited

OTHER PUBLICATIONS

Brandenburg, et al., Phase Diagram of Deep Rough Mutant Lipopolysaccharide from Salmonella Minnesota R595, Journal of Structural Biology, 93(2):93-106 (1992).
Dorland's Illustrated Medical Dictionary, W.B. Sanders Company, 25th Ed. (1974).
Sabroe et al., JI P1630-635 (2003).
Dalsgaard et al., Saponin adjuvants, Archiv. Fur die gesamte Virusforschung, vol. 44: 243-254 (1974).
R. Gluck, Vaccine, 10:915-920 (1992).
Rubins, et al., Microbial Pathogenesis.
Robbins and Kawakami, Current Opinions in Immunology, 8:628-636 (1996).
Van den Eynde et al., International Journal of Clinical & Laboratory Research submitted 1997.
Correale et al., Journal of the National Cancer Institute 89: 293 (1997).
Singh, M., et al., Recent Advances in Vaccine Adjuvants, Pharmaceutical Research, Jun. 6, 2002, vol. 19, No. 6, pp. 715-728.
Fluarix product information sheet, Fluarix SH 2005 English, 2005.

\* cited by examiner

FIG. 1 - Geometric mean titers (GMTs) for anti-HA antibody at different timepoints (ATP cohort for immunogenicity)
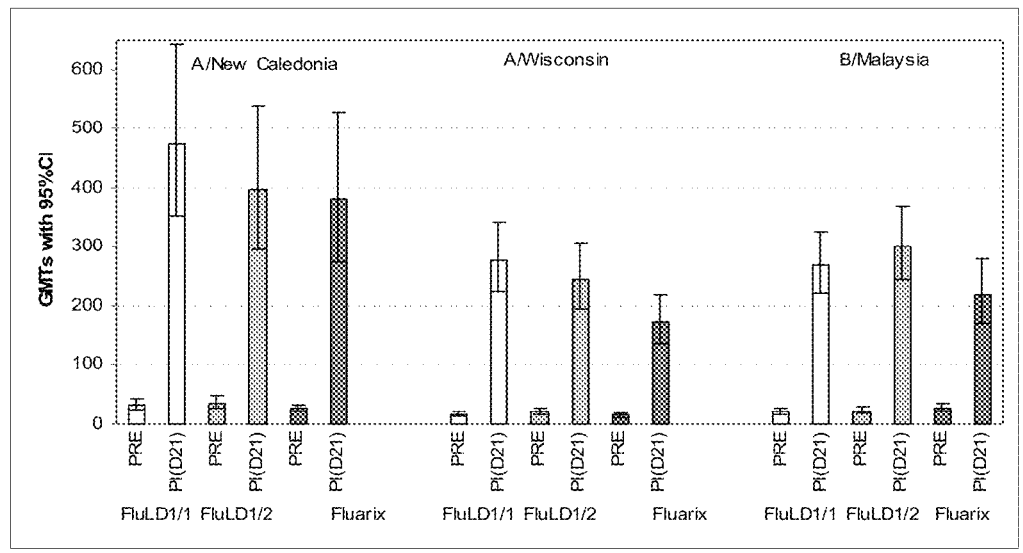
FIG. 2 - SPR for HI antibody titer with 95% confidence interval at day 0 and day 21 (ATP cohort for immunogenicity)
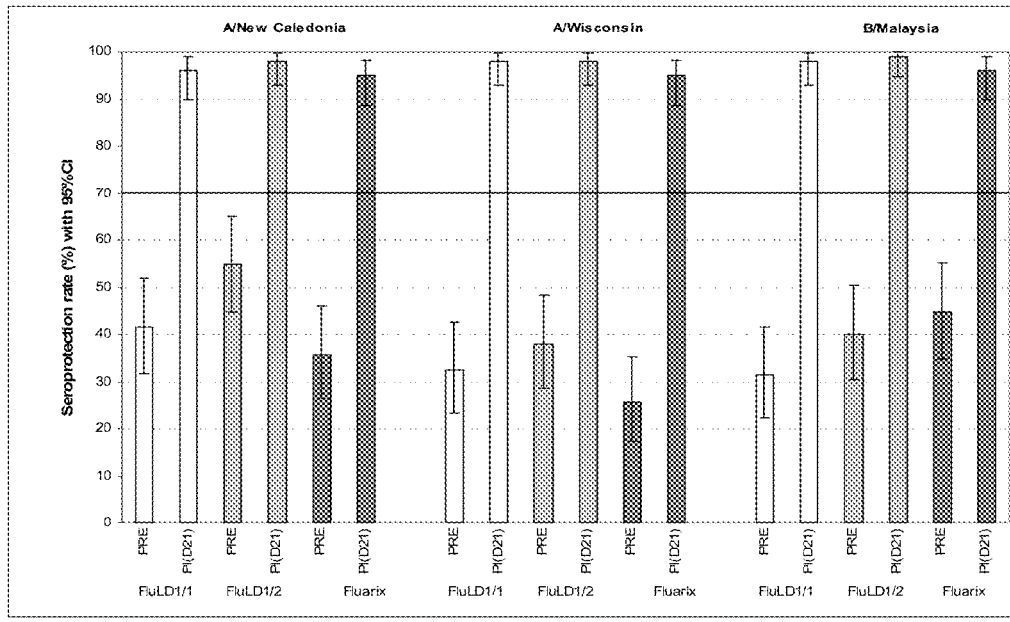

FIG. 3 - SCR for HI antibody titer with 95% confidence interval at day 21 (ATP cohort for immunogenicity)
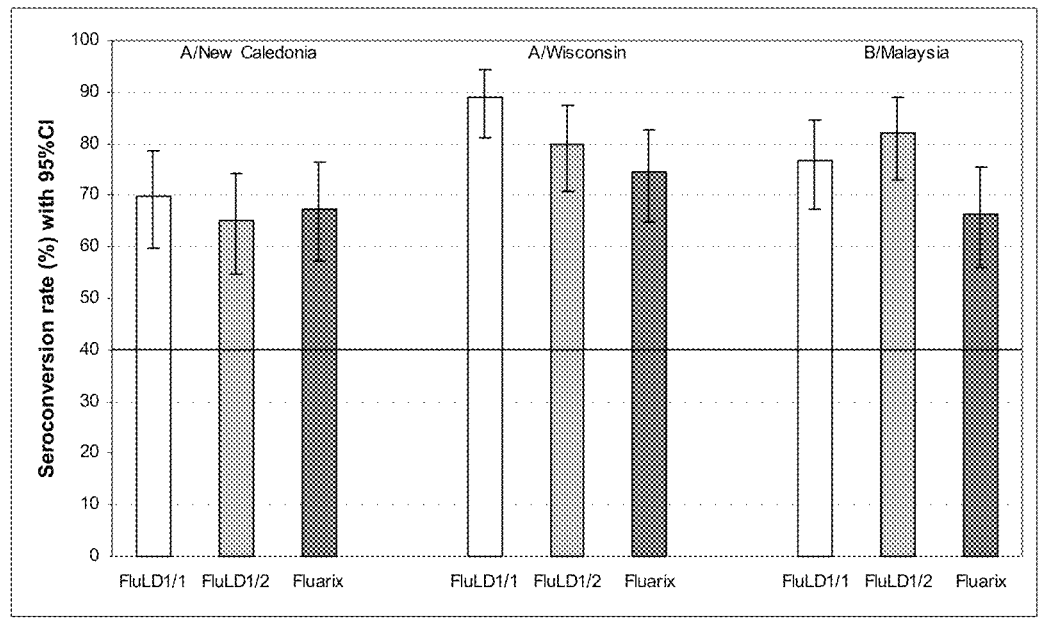
FIG. 4 - SCF for HI antibody titer with 95% confidence interval at day 21 (ATP cohort for immunogenicity)
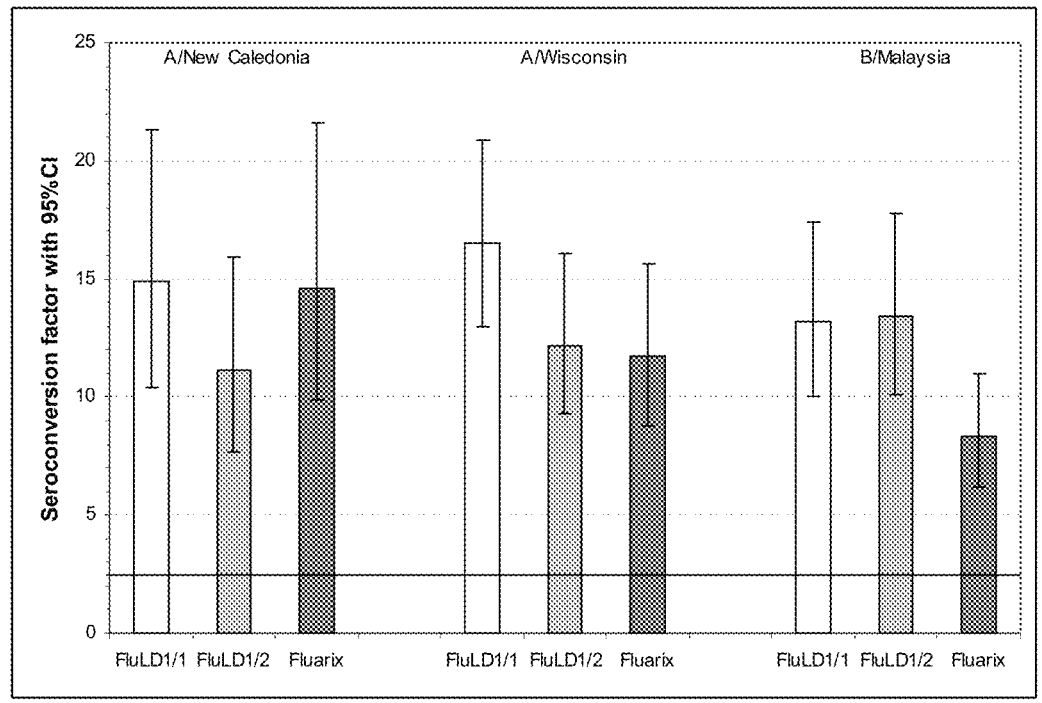

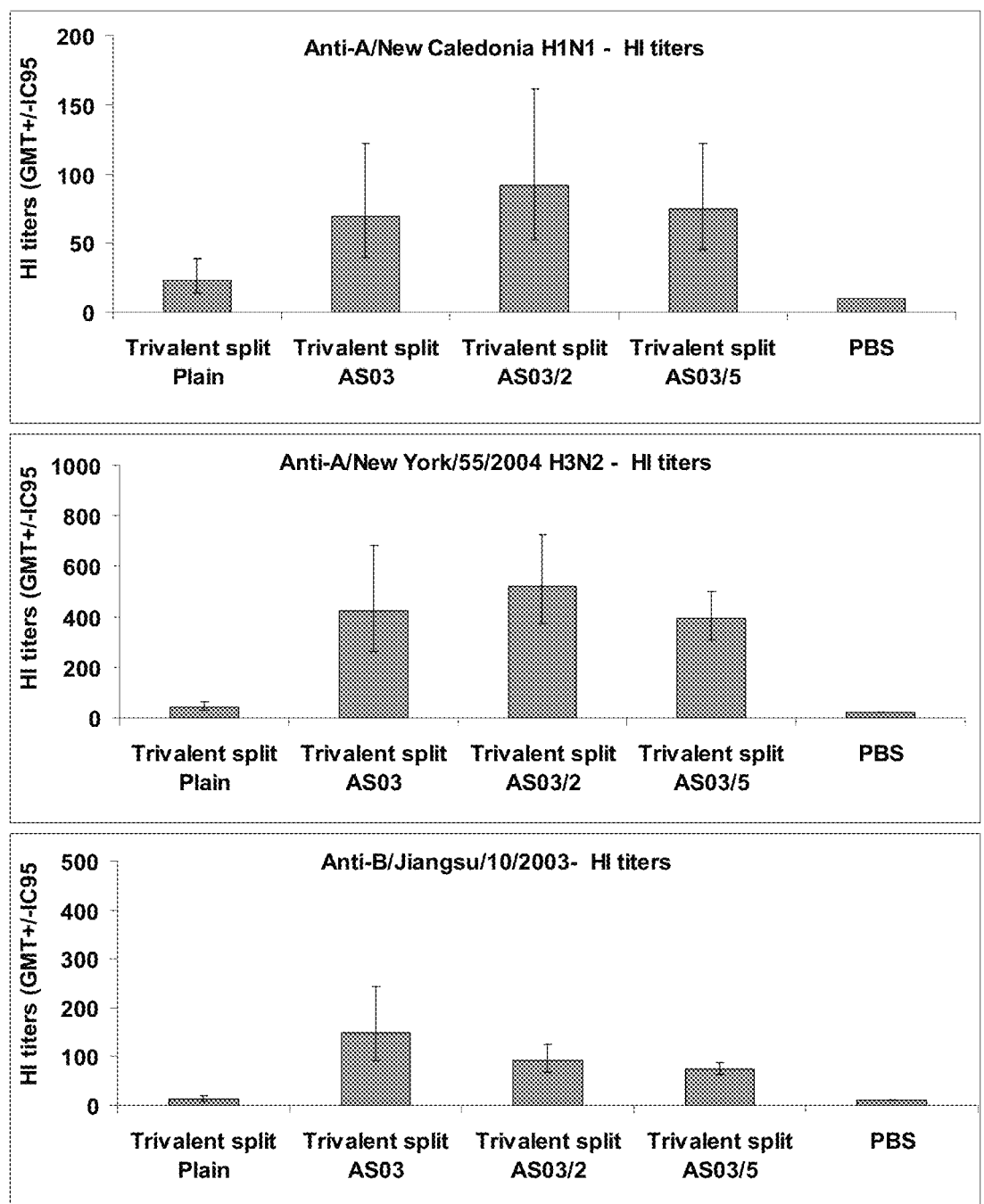
FIG. 6   Haemagglutinin Inhibition test (GMT +/- IC95) in C57Bl/6 mice primed with heterosubtypic strains (dose range AS03)

FIG. 7    Cellular immune response (CD4+ T cell) in PBMC from C57Bl/6 mice primed with heterosubtypic strains (dose range AS03)
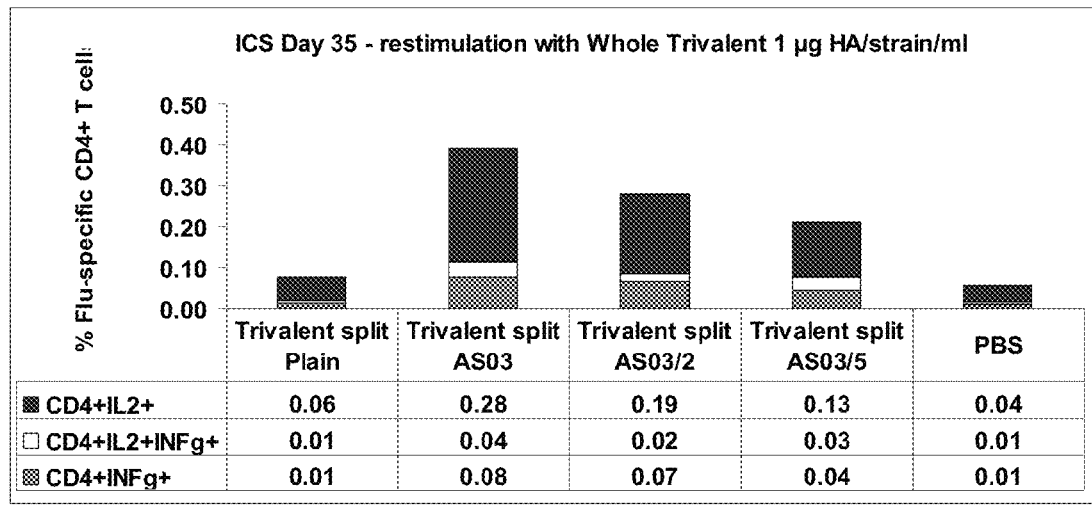
FIG. 8    Cellular immune response (CD4+ T cell) in PBMC from C57Bl/6 mice primed with heterosubtypic strains and immunized with low dose antigen (0.5 µg) adjuvanted with dose range AS03
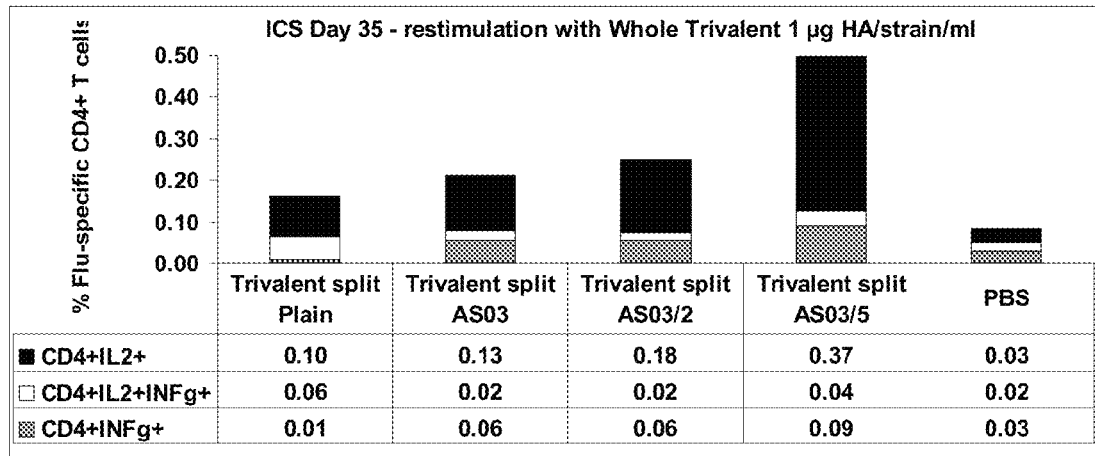

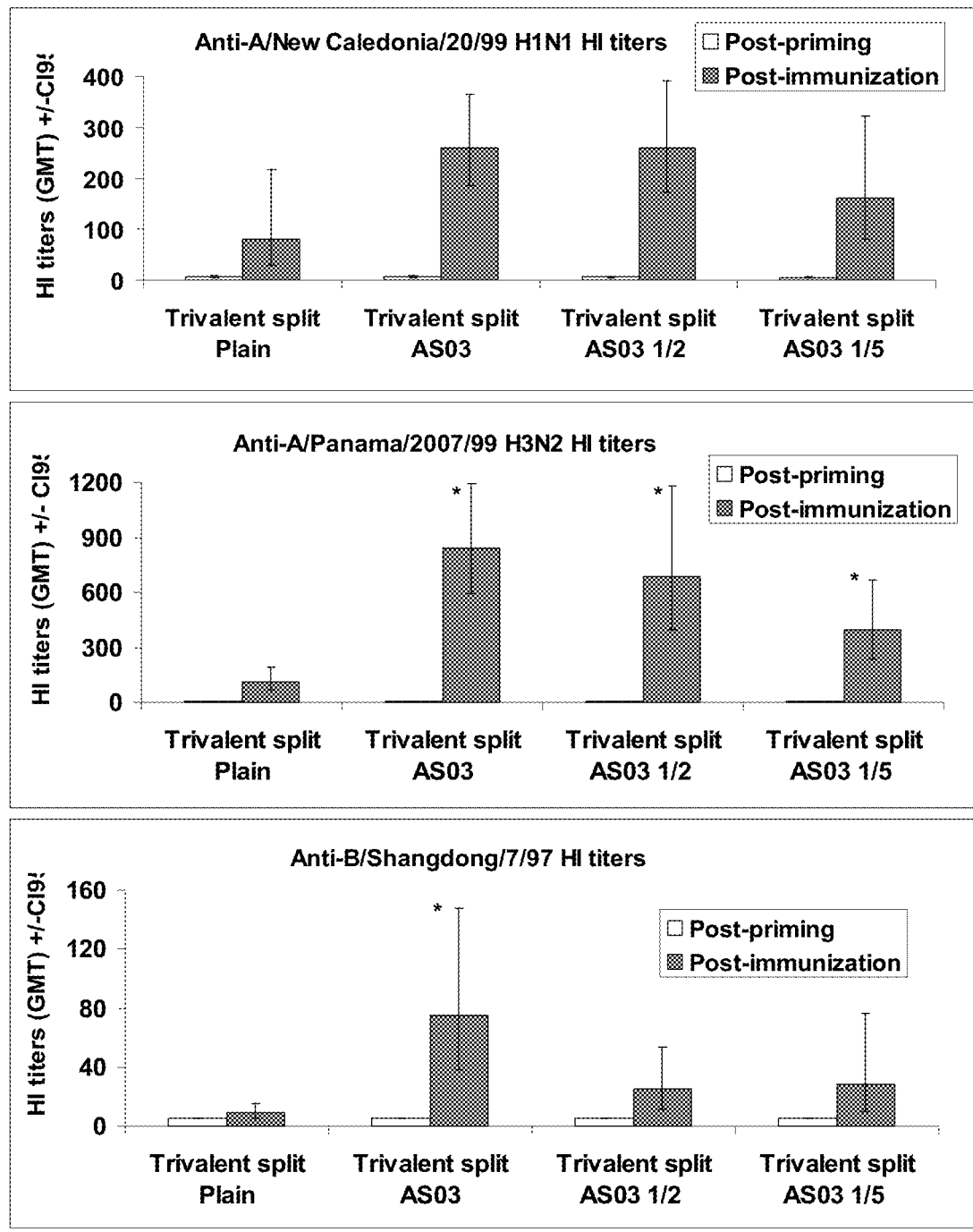
FIG. 12  Haemagglutinin Inhibition test (GMT +/- IC95) in pigs primed with homologous strains (dose range AS03)
* Group with statistically significant difference compared to the plain.

VACCINE COMPRISING AN OIL IN WATER EMULSION

This application is filed pursuant to 35 USC 371 as a United States National Phase Application of International Patent Application Serial No. PCT/EP2007/060743 filed on Oct. 10, 2007, which claims the priority of GB 0620336.8 filed on Oct. 12, 2006, GB 0620337.6 filed Oct. 12, 2006, GB 620815.1 filed on Oct. 19, 2006, GB 0620816.9 filed Oct. 19, 2006, all filed in the United Kingdom, PCT/EP2006/069977 filed Dec. 20, 2006, PCT/EP2006/069979 filed Dec. 20, 2006, GB 0707697.9 filed Apr. 20, 2007 in the United Kingdom, GB 0711357 filed Jun. 12, 2007 filed in the United Kingdom, and GB 0712062.9 filed Jun. 21, 2007 filed in the United Kingdom.

TECHNICAL FIELD

The present invention relates to improved vaccine and immunogenic compositions and their use in medicine. In particular the invention relates to vaccine or immunogenic formulations comprising an oil-in-water emulsion adjuvant and their use in medicine, in particular their use in augmenting immune responses to various antigens, and to methods of preparation, wherein the oil in water emulsion comprises a tocol, a metabolisable oil and an emulsifying agent.

TECHNICAL BACKGROUND

New compositions or vaccines with an improved immunogenicity are always needed. As one strategy, adjuvants have been used to try and improve the immune response raised to any given antigen and/or reduce reactogenicity/toxicity in the host.

Oil in water emulsions per se are well known in the art, and have been suggested to be useful as adjuvant compositions (EP 399843; WO 95/17210).

WO95/17210 discloses oil in water emulsions comprising from 2 to 10% squalene, from 2 to 10% alpha tocopherol and from 0.3 to 3% tween 80 and their use alone or in combination with QS21 and/or 3D-MPL.

WO99/12565 discloses oil in water emulsion compositions comprising a metabolisable oil, a saponin and a sterol. The oil in water emulsions further comprise 3D-MPL.

WO99/11241 discloses oil in water emulsions comprising metabolisable oil and a saponin, wherein the oil and saponin are present in a ratio of between 1:1 and 200:1.

There is still a need for improved vaccine and immunogenic compositions that provide a suitable immune response and are less reactogenic in the host.

STATEMENT OF THE INVENTION

The present inventors have discovered vaccine or immunogenic compositions comprising lower amounts of each component of the oil in water emulsion may be used whilst still maintaining a comparable immune response against an antigen or antigenic composition within said composition. This carries the advantage maintaining the level of immunogenicity against an antigen whilst the reactogenicity within the host recipient is reduced.

Accordingly, in the first aspect of the present invention there is provided an immunogenic composition comprising an antigen or antigenic composition, and an adjuvant composition comprising an oil-in-water emulsion, wherein said oil-in-water emulsion comprises 0.5-10 mg metabolisable oil, 0.5-11 mg tocol and 0.4-4 mg emulsifying agent, per human dose.

In another aspect of the present invention, there is provided a vaccine composition comprising an antigen or antigenic composition, and an adjuvant composition comprising an oil-in-water emulsion, wherein said oil-in-water emulsion comprises 0.5-10 mg metabolisable oil, 0.5-11 mg tocol and 0.4-4 mg emulsifying agent, per human dose.

In a further aspect of the invention there is provided the use of a vaccine or immunogenic composition comprising an antigen or antigenic composition, and an adjuvant composition comprising an oil-in-water emulsion wherein said oil-in-water emulsion comprises 0.5-10 mg metabolisable oil, 0.5-11 mg tocol and 0.4-4 mg emulsifying agent in the manufacture of an immunogenic composition for the prevention of infection and/or disease.

In a further aspect, there is provided a method or use as hereinabove defined, for protection against infection or disease caused by a pathogen which is a variant of the pathogen from which the antigen in the immunogenic composition is derived. In another embodiment, there is provided a method or use as hereinabove defined for protection against infections or disease caused by a pathogen which comprises an antigen which is a variant of that antigen in the immunogenic composition.

BRIEF DESCRIPTION OF FIGURES

FIG. 1: Clinical trial: geometric mean titers (GMTs) for anti-HA antibody at different timepoints (ATP cohort for immunogenicity).

FIG. 2: Clinical trial: seroprotection rate (SPR) for HI antibody titer with 95% confidence interval at day 0 and day 21 (ATP cohort for immunogenicity).

FIG. 3: Clinical trial: seroconversion rate (SCR) for HI antibody titer with 95% confidence interval at day 21 (ATP cohort for immunogenicity).

FIG. 4: Clinical trial: seroconversion factor (SCF) for HI antibody titer with 95% confidence interval at day 21 (ATP cohort for immunogenicity).

FIGS. 5A-5C: Results of Mice study: Haemagglutinin Inhibition test (GMT+/−IC95) in BALB/c mice primed with heterosubtypic strains (dose range AS03) wherein FIG. 5A shows Anti-A/New Caledonia/20/99 HI titers; FIG. 5B shows Anti-A/Panama/2007/99 HI titers and FIG. 5C shows Anti-B/Shandong/7/97 HI titers.

FIG. 6: Mice study: Haemagglutinin Inhibition test (GMT+/−IC95) in C57Bl/6 mice primed with heterosubtypic strains (dose range AS03).

FIG. 7: Mice study: Cellular immune response (CD4+ T cell) in PBMC from C57Bl/6 mice primed with heterosubtypic strains (dose range AS03).

FIG. 8: Mice study: Cellular immune response (CD4+ T cell) in PBMC from C57Bl/6 mice primed with heterosubtypic strains and immunized with low dose antigen (0.5 µg) adjuvanted with dose range AS03.

Figures 9A, 9B:
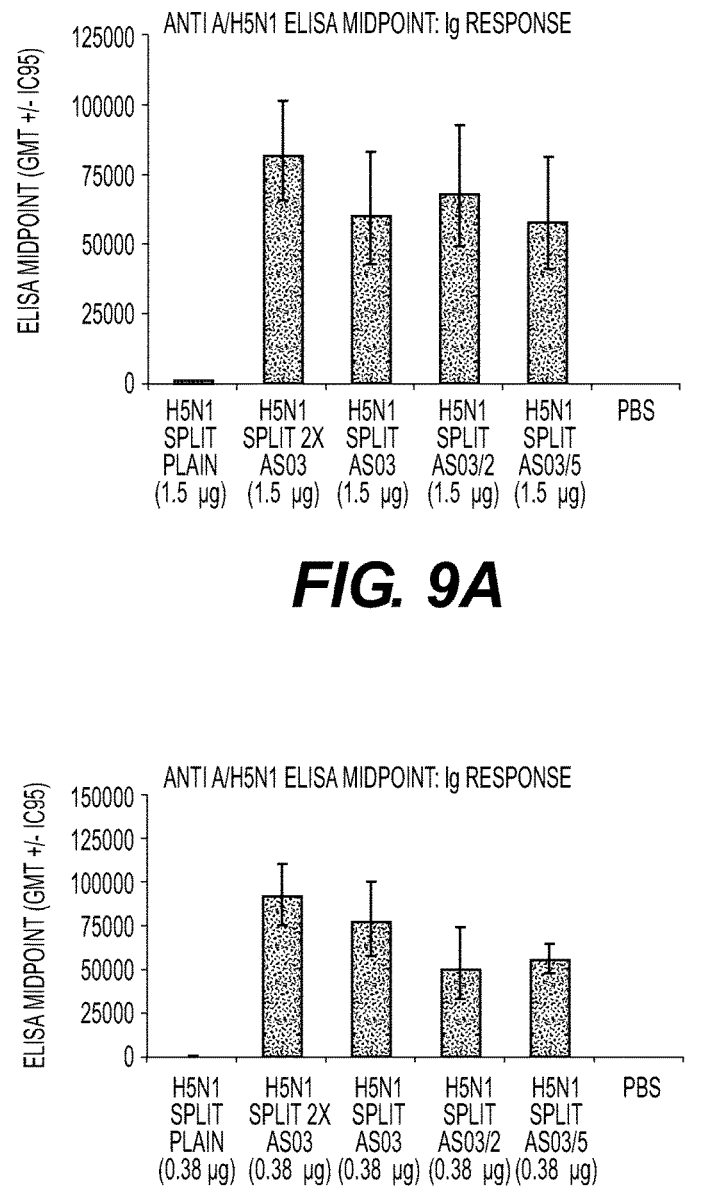

FIGS. 9A-9F: Results Mice study: H5N1-specific serum Ig ELISA titers (FIGS. A and B) and anti-H5N1 IgG1 (FIGS. C and D) and IgG2b (FIGS. E and F) isotypic responses on day 14 post-immunization (GMT+/−IC95) for two different antigen dose: 1.5 µg (FIGS. A, C and E) or 0.38 µg (FIGS. B, D and F)

Figures 10A, 10B:
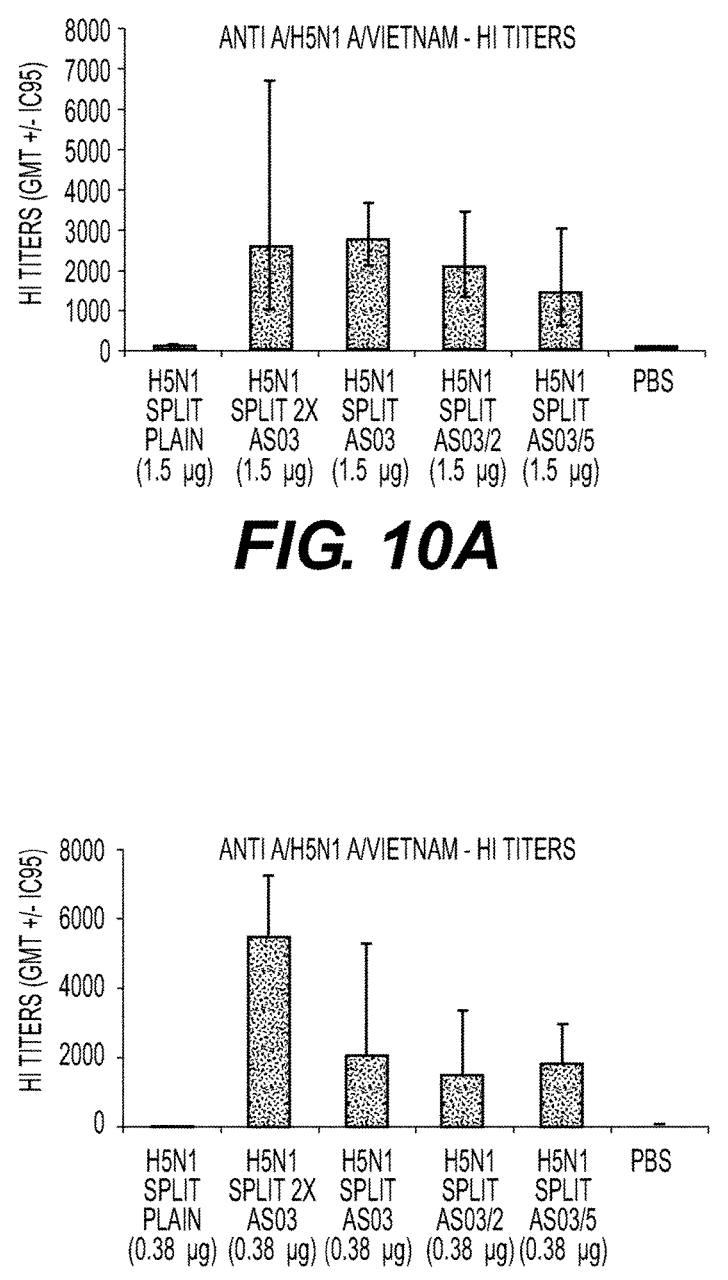

FIGS. 10A and 10B: Results Mice study: Hemagglutination inhibition test (GMT+/−IC95) on day 21 post-immunization (GMT+/−IC95) for two different antigen dose: 1.5 µg (FIG. A) or 0.38 µg (FIG. B).

FIG. 12: Pigs study. Haemagglutinin Inhibition test (GMT+/−1-IC95) in pigs primed with homologous strains (dose range AS03).

DETAILED DESCRIPTION OF THE INVENTION

Figure 5A:
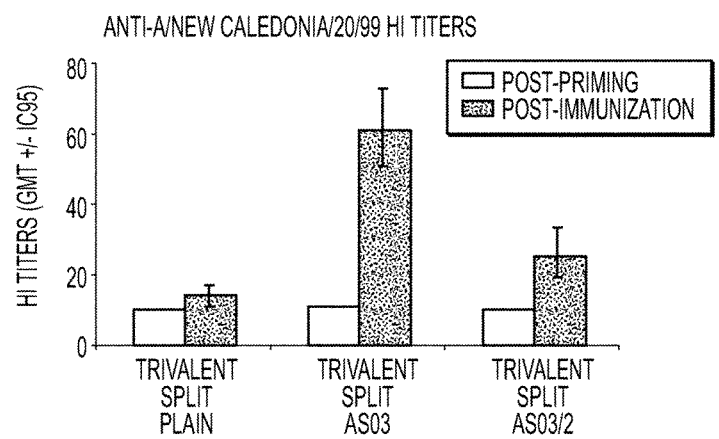

The terms "comprising", "comprise" and "comprises" herein are intended by the inventors to be optionally substitutable with the terms "consisting of", "consist of" and "consists of", respectively, in every instance.

Embodiments herein relating to "vaccine compositions" of the invention are also applicable to embodiments relating to "immunogenic compositions" of the invention, and vice versa.

In one embodiment of the invention there is provided a vaccine or immunogenic composition comprising an antigen or antigen composition and an adjuvant composition consisting of an oil in water emulsion, wherein said oil in water emulsion comprises 0.5-10 mg metabolisable oil, 0.5-11 mg tocol and 0.4-4 mg emulsifying agent, per human dose.

In a further embodiment of the invention there is provided a vaccine or immunogenic composition comprising an antigen or antigen composition and an adjuvant composition comprising an oil in water emulsion, wherein the oil in water emulsion comprises 0.5-10 mg metabolisable oil, (such as squalene), 0.5-11 mg tocol (such as alpha-tocopherol and 0.4-4 mg emulsifying agent (such as polyoxyethylene sorbitan monooleate), per human dose.

Oil in Water Emulsion Component

The adjuvant composition of the invention comprises an oil-in-water emulsion adjuvant, preferably said emulsion comprises a metabolisable oil in an amount of 0.5-10 mg, a tocol in an amount of 0.5-11 mg and an emulsifying agent in an amount of 0.4-4 mg and having oil droplets of which at least 70% by intensity have diameters of less than 1 µm.

In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W. B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10th Edition, entry no. 8619).

Suitably the metabolisable oil is present in the adjuvant composition in an amount of 0.5-10 mg, preferably 1-10, 2-10, 3-9, 4-8, 5-7, or 5-6 mg (e.g. 2-3, 5-6, or 9-10 mg), specifically 5.35 mg or 2.14 mg. In a further embodiment of the invention, the metabolisable oil is present in the vaccine (or immunogenic) composition in an amount of 0.5-10 mg, preferably 1-10, 2-10, 3-9, 4-8, 5-7, or 5-6 mg (e.g. 2-3, 5-6, or 9-10 mg), specifically 5.35 mg or 2.14 mg.

The amount of metabolisable oil in vaccine or immunogenic composition may be expressed as a percentage of the total composition. Suitably the metabolisable oil is present in the vaccine composition in an amount of 0.5% to 2%, preferably 0.25-2, or 0.25-1.75, or 0.5-1.65, or 0.6-1.5, or 0.8-1.4 or 1-1.25% (v/v) oil of the total composition volume.

In another specific embodiment, the metabolisable oil is present in a final amount of about 1.25% of the total volume of the vaccine (or immunogenic) composition. In another specific embodiment, the metabolisable oil is present in a final amount of 0.25% (v/v) of the total composition volume.

By way of clarification, concentrations given in v/v can be converted into concentration in w/v by applying the following conversion factor: a 5% (v/v) squalene concentration is equivalent to a 4.28% (w/v) squalene concentration.

The oil in water emulsion comprises a tocol. Tocols are well known in the art and are described in EP0382271. Suitably the tocol is alpha-tocopherol or a derivative thereof such as alpha-tocopherol succinate (also known as vitamin E succinate). Said tocol is suitably present in the adjuvant composition in an amount of 0.5-11 mg, preferably 1-11, 2-10, 3-9, 4-8, 5-7, 5-6 (e.g. 10-11, 5-6, 2.5-3.5 or 1-3 mg). In a specific embodiment the tocol is present in an amount of 5.94 mg or 2.38 mg. In a further embodiment, said tocol is suitably present in the vaccine (or immunogenic) composition in an amount of 0.5-11 mg, preferably 1-11, 2-10, 3-9, 4-8, 5-7, 5-6 (e.g. 10-11, 5-6, 2.5-3.5 or 1-3 mg). In a specific embodiment the tocol is present in an amount of 5.94 mg or 2.38 mg.

The amount of tocol may be expressed as a percentage of the total vaccine or immunogenic composition volume. Suitably tocol is present in the vaccine composition in an amount 0.25% to 2% (v/v) of the total volume of the immunogenic composition, preferably at 0.25-2 comprises 0.25-2, or 0.25-1.75, or 0.5-1.65, or 0.6-1.5, or 0.8-1.4 or 1-1.25 (v/v) tocol of the total volume.

Preferably tocol is present in an amount of between 0.2% and 2% (v/v) of the total volume of the vaccine (or immunogenic) composition, more preferably at an amount of 1.25% (v/v) in a 0.5 ml dose volume.

In a specific embodiment, the tocol is present in a final amount of about 1.25% of the total volume of the vaccine or immunogenic composition. In another specific embodiment, the tocol is present in a final amount of 0.25% (v/v) of the total volume or 1.25% (v/v) in 0.5 ml dose volume or 0.9% (v/v), in 0.7 ml dose volume, or 0.5% (v/v) in 0.5 ml dose or 0.35-0.37%, preferably 0.36% in 0.7 ml vaccine or immunogenic dose.

By way of clarification, concentrations given in v/v can be converted into concentration in w/v by applying the following conversion factor: a 5% (v/v) alpha-tocopherol concentration is equivalent to a 4.8% (w/v) alpha-tocopherol concentration.

The oil in water emulsion further comprises an emulsifying agent. The emulsifying agent may suitably be polyoxyethylene sorbitan monooleate. In a particular embodiment the emulsifying agent may be selected from the group comprising: Polysorbate® 80 or Tween® 80.

Said emulsifying agent is suitably present in the adjuvant composition in an amount of 0.1-5, 0.2-5, 0.3-4, 0.4-3 or 2-3 mg (e.g. 0.4-1.2, 2-3 or 4-5 mg) emulsifying agent. In a specific embodiment the emulsifying agent is present in an amount of 0.97 mg or 2.425 mg.

Further, said emulsifying agent is suitably present in the vaccine or immunogenic composition in an amount of 0.1-5, 0.2-5, 0.3-4, 0.4-3 or 2-3 mg (e.g. 0.4-1.2, 2-3 or 4-5 mg) emulsifying agent. In a specific embodiment the emulsifying agent is present in an amount of 0.97 mg or 2.425 mg.

The amount of emulsifying agent may be expressed as a percentage of the total vaccine or immunogenic composition volume. Suitably the emulsifying agent is present in the vaccine (or immunogenic) composition in an amount 0.125-0.8% (v/v) of the total volume of the composition, preferably at 0.08-0.05, or 0.1-0.7, or 0.2-0.6, or 0.25-0.55, or 0.3-0.52 or 0.4-0.5% (v/v) of the total volume. In a specific embodiment the emulsifying agent is present in an amount of 1%, 0.5% or 0.2% (v/v) of the total vaccine or immunogenic composition volume.

By way of clarification, concentrations given in v/v can be converted into concentration in w/v by applying the following conversion factor: a 1.8% (v/v) polysorbate 80 concentration is equivalent to a 1.91% (w/v) polysorbate 80 concentration.

In a specific embodiment, a 0.5 ml vaccine or immunogenic dose volume contains 0.45% (v/v) Tween 80, and a 0.7 ml dose volume contains 0.315% (v/v) Tween 80. In another specific embodiment a 0.5 ml dose contains 0.18% (v/v) emulsifying agent and a 0.7 ml vaccine or immunogenic composition dose contains 0.126% (v/v) emulsifying agent.

By the term "human dose" is meant a dose which is in a volume suitable for human use. Generally this is between 0.25 and 1.5 ml. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the paediatric population, a human dose may be less than 0.5 ml such as between 0.25 and 0.5 ml. The invention is characterised in that each or all of the individual components of the adjuvant within the immunogenic composition is/are at a lower level than previously thought useful and is/are typically as recited above. Particularly suitable compositions comprise the following adjuvant components in the following amounts are in a final volume of human dose of 0.5 ml:

antigen composition to provide the final human dose of vaccine. The final volume of such dose will of course vary dependent on the initial volume of the adjuvant composition and the volume of antigen composition added to the adjuvant composition. In an alternative embodiment, liquid adjuvant is used to reconstitute a lyophilised antigen composition. In this embodiment, the human dose suitable volume of the adjuvant composition is approximately equal to the final volume of the human dose. The liquid adjuvant composition is added to the vial containing the lyophilised antigen composition. The final human dose can vary between 0.5 and 1.5 ml.

The method of producing oil-in-water emulsions is well known to the person skilled in the art. Commonly, the method comprises mixing the tocol-containing oil phase with a surfactant such as a PBS/TWEEN80™ solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil in water emulsion, the oil and emulsifier should be in an aqueous carrier. The aqueous carrier may be, for example, phosphate buffered saline.

Preferably the oil-in-water emulsion systems of the present invention have a small oil droplet size in the sub-micron range. Suitably the droplet sizes will be in the range 120 to 750 nm, more preferably sizes from 120 to 600 nm in diameter. Most preferably the oil-in water emulsion contains oil droplets of which at least 70% by intensity are less than 500 nm in diameter, more preferably at least 80% by intensity are less than 300 nm in diameter, more preferably at least 90% by intensity are in the range of 120 to 200 nm in diameter.

TABLE 1

|  | Adjuvant A | Adjuvant B | Adjuvant E | Adjuvant F | Adjuvant C | Adjuvant G | Adjuvant D |
|---|---|---|---|---|---|---|---|
| o/w emulsion | 125 μl | 100 μl | 83.33 μl | 62.5 μl | 50 μl | 31.25 μl | 25 μl |
| | | | | Components: | | | |
| Tocopherol | 5.94 mg | 4.28 mg | 3.57 mg | 2.68 mg | 2.38 mg | 1.34 mg | 1.19 mg |
| Squalene | 5.35 mg | 4.75 mg | 3.96 mg | 2.97 mg | 2.14 mg | 1.49 mg | 1.07 mg |
| Polysorbate 80 | 2.43 mg | 1.94 mg | 1.62 mg | 1.21 mg | 0.97 mg | 0.61 mg | 0.48 mg |

The invention further provides an adjuvant composition comprising the individual components as defined herein above and in the amount defined above, for example but not exclusively as illustrated in Table 1. Typically such an adjuvant composition will be in a human dose suitable volume. Where the adjuvant is in a liquid form to be combined with a liquid form of an antigenic composition, the adjuvant composition will be in a human dose suitable volume which is a fraction of the intended final volume of the human dose, such as for example approximately half of the intended final volume of the human dose, for example a 350 μl volume for an intended human dose of 0.7 ml, or a 250 μl volume for an intended human dose of 0.5 ml. The adjuvant composition is diluted when combined with the The oil droplet size, i.e. diameter, according to the present invention is given by intensity. There are several ways of determining the diameter of the oil droplet size by intensity. Intensity is measured by use of a sizing instrument, suitably by dynamic light scattering such as the Malvern Zetasizer 4000 or preferably the Malvern Zetasizer 3000HS. A detailed procedure is given in Example 11.2. A first possibility is to determine the z average diameter ZAD by dynamic light scattering (PCS-Photon correlation spectroscopy); this method additionally give the polydispersity index (PDI), and both the ZAD and PDI are calculated with the cumulants algorithm. These values do not require the knowledge of the particle refractive index. A second mean is to calculate the diameter of the oil droplet by determining the whole particle size distribution by another algorithm, either the Contin, or NNLS, or the automatic "Malvern" one (the default algorithm provided for by the sizing instrument). Most of the time, as the particle refractive index of a complex composition is unknown, only the intensity distribution is taken into consideration, and if necessary the intensity mean originating from this distribution.

Optional Immunostimulants

In a further embodiment of the invention there is provided a vaccine or immunogenic composition comprising an antigen or antigen composition and an adjuvant composition comprising an oil in water emulsion and optionally one or more further immunostimulants, wherein said oil in water emulsion comprises 0.5-10 mg metabolisable oil, 0.5-11 mg tocol and 0.4-4 mg emulsifying agent.

In one embodiment the adjuvant composition comprises an oil and water emulsion as described herein. In a further embodiment the adjuvant composition may further comprise one or more additional adjuvants or immunostimulants. In a further embodiment the adjuvant composition optionally comprises one or more additional adjuvants or immunostimulants other than QS21 and/or MPL.

The optional additional adjuvant is selected from the group: a saponin, lipid A or a derivative thereof, an immunostimulatory oligonucleotide, an alkyl glucosaminide phosphate, a metal salt, a toll-like receptor agonist or combinations thereof. It is preferred that the adjuvant is a Toll like receptor agonist in particular an agonist of a Toll like receptor 2, 3, 4, 7, 8 or 9, or a saponin. It is further preferred that the adjuvant system comprises two or more adjuvants from the above list. Combinations preferably contain a saponin (in particular QS21) adjuvant and/or a Toll like receptor 4 against such as 3D-MPL or a Toll like receptor 9 agonist such as a CpG containing immunostimulatory oligonucleotide. Other preferred combinations comprise a saponin (in particular QS21) and a Toll like receptor 4 agonist such as a saponin (in particular QS21) and a Toll like receptor 4 ligand such as 3D-MPL or an alkyl glucosaminide phosphate.

In an embodiment the additional adjuvant is a Toll like receptor (TLR) 4 ligand, preferably an agonist such as a lipid A derivative particularly monophosphoryl lipid A or more particularly 3 Deacylated monophoshoryl lipid A (3 D-MPL).

3D-MPL is available under the trademark MPL® by GlaxoSmithKline Biologicals North America and primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3 D-MPL is used. Small particle 3 D -MPL has a particle size such that it may be sterile-filtered through a 0.22 μm filter. Such preparations are described in International Patent Application No. WO 94/21292. Synthetic derivatives of lipid A are known and thought to be TLR 4 agonists including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S, 9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenphosphate) (WO99/64301 and WO 00/0462)

OM 197 MP-Ac DP (3S-, 9R)-3-[(R)-dodecanoyloxytetra-decanoylamino]-4-oxo-5-aza-9-[(R)-3-hydroxytetradecanoylamino]decan-1,10-diol,1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

Other suitable TLR-4 ligands, capable of causing a signalling response through TLR-4 (Sabroe et al, JI 2003 p 1630-5) are, for example, lipopolysaccharide from gram-negative bacteria and its derivatives, or fragments thereof, in particular a non-toxic derivative of LPS (such as 3D-MPL). Other suitable TLR agonist are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, muramyl dipeptide (MDP) or F protein of respiratory syncitial virus. In one embodiment the TLR agonist is HSP 60, 70 or 90.

Toll-like receptors (TLRs) are type I transmembrane receptors, evolutionarily conserved between insects and humans. Ten TLRs have so far been established (TLRs 1-10) (Sabroe et al, JI 2003 p 1630-5). Members of the TLR family have similar extracellular and intracellular domains; their extracellular domains have been shown to have leucine—rich repeating sequences, and their intracellular domains are similar to the intracellular region of the interleukin—1 receptor (IL-1R). TLR cells are expressed differentially among immune cells and other cells (including vascular epithelial cells, adipocytes, cardiac myocytes and intestinal epithelial cells). The intracellular domain of the TLRs can interact with the adaptor protein Myd88, which also posses the IL-1R domain in its cytoplasmic region, leading to NF-KB activation of cytokines; this Myd88 pathway is one way by which cytokine release is effected by TLR activation. The main expression of TLRs is in cell types such as antigen presenting cells (eg dendritic cells, macrophages etc).

Activation of dendritic cells by stimulation through the TLRs leads to maturation of dendritic cells, and production of inflammatory cytokines such as IL-12. Research carried out so far has found that TLRs recognise different types of agonists, although some agonists are common to several TLRs. TLR agonists are predominantly derived from bacteria or viruses, and include molecules such as flagellin or bacterial lipopolysaccharide (LPS).

By "TLR agonist" it is meant a component which is capable of causing a signalling response through a TLR signalling pathway, either as a direct ligand or indirectly through generation of endogenous or exogenous ligand (Sabroe et al, JI 2003 p 1630-5).

In another embodiment, other natural or synthetic agonists of TLR molecules are used as optional additional immunostimulants. These could include, but are not limited to agonists for TLR2, TLR3, TLR7, TLR8 and TLR9.

In one embodiment of the present invention, a TLR agonist is used that is capable of causing a signalling response through TLR-1 (Sabroe et al, JI 2003 p 1630-5). Suitably, the TLR agonist capable of causing a signalling response through TLR-1 is selected from: Tri-acylated lipopeptides (LPs); phenol-soluble modulin; Mycobacterium tuberculosis LP; S-(2,3-bis(palmitoyloxy)-(2-RS)-propyl)-N-palmitoyl-(R)-Cys-(S)-Ser-(S)-Lys(4)-OH, trihydrochloride (Pam₃Cys) LP which mimics the acetylated amino terminus of a bacterial lipoprotein and OspA LP from *Borrelia burgdorfei*.

In an alternative embodiment, a TLR agonist is used that is capable of causing a signalling response through TLR-2 (Sabroe et al, JI 2003 p 1630-5). Suitably, the TLR agonist capable of causing a signalling response through TLR-2 is one or more of a lipoprotein, a peptidoglycan, a bacterial lipopeptide from *M tuberculosis, B burgdorferi. T pallidum*; peptidoglycans from species including Staphylococcus aureus; lipoteichoic acids, mannuronic acids, *Neisseria porins*, bacterial fimbriae, *Yersina* virulence factors, CMV virions, measles haemagglutinin, and zymosan from yeast.

In an alternative embodiment, a TLR agonist is used that is capable of causing a signalling response through TLR-3 (Sabroe et al, JI 2003 p 1630-5). Suitably, the TLR agonist capable of causing a signalling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signalling response through TLR-5 (Sabroe et al, JI 2003 p 1630-5). Suitably, the TLR agonist capable of causing a signalling response through TLR-5 is bacterial flagellin.

In an alternative embodiment, a TLR agonist is used that is capable of causing a signalling response through TLR-6 (Sabroe et al, JI 2003 p 1630-5). Suitably, the TLR agonist capable of causing a signalling response through TLR-6 is mycobacterial lipoprotein, di-acylated LP, and phenol-soluble modulin. Further TLR6 agonists are described in WO2003043572.

In an alternative embodiment, a TLR agonist is used that is capable of causing a signalling response through TLR-7 (Sabroe et al, JI 2003 p 1630-5). Suitably, the TLR agonist capable of causing a signalling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO02085905.

In an alternative embodiment, a TLR agonist is used that is capable of causing a signalling response through TLR-8 (Sabroe et al, JI 2003 p 1630-5). Suitably, the TLR agonist capable of causing a signalling response through TLR-8 is a single stranded RNA (ssRNA), an imidazoquinoline molecule with anti-viral activity, for example resiquimod (R848); resiquimod is also capable of recognition by TLR-7. Other TLR-8 agonists which may be used include those described in WO2004071459.

Immunostimulatory oligonucleotides or any other Toll-like receptor (TLR) 9 agonist may also be used. The preferred oligonucleotides for use in adjuvants or vaccines or immunogenic compositions of the present invention are CpG containing oligonucleotides, preferably containing two or more dinucleotide CpG motifs separated by at least three, more preferably at least six or more nucleotides. A CpG motif is a Cytosine nucleotide followed by a Guanine nucleotide. The CpG oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. No. 5,666,153, U.S. Pat. No. 5,278, 302 and WO95/26204.

Examples of preferred oligonucleotides have the following sequences. The sequences preferably contain phosphorothioate modified internucleotide linkages.

```
OLIGO 1(SEQ ID NO: 1):
TCC ATG ACG TTC CTG ACG TT  (CpG 1826)

OLIGO 2 (SEQ ID NO: 2):
TCT CCC AGC GTG CGC CAT  (CpG 1758)

OLIGO 3(SEQ ID NO: 3):
ACC GAT GAC GTC GCC GGT GAC GGC ACC ACG

OLIGO 4 (SEQ ID NO: 4):
TCG TCG TTT TGT CGT TTT GTC GTT  (CpG 2006)

OLIGO 5 (SEQ ID NO: 5):
TCC ATG ACG TTC CTG ATG CT  (CpG 1668)

OLIGO 6 (SEQ ID NO: 6):
TCG ACG TTT TCG GCG CGC GCC G  (CpG 5456)
```

Alternative CpG oligonucleotides may comprise the preferred sequences above in that they have inconsequential deletions or additions thereto. The CpG oligonucleotides utilised in the present invention may be synthesized by any method known in the art (for example see EP 468520). Conveniently, such oligonucleotides may be synthesized utilising an automated synthesizer.

Accordingly, in another embodiment, the adjuvant composition further comprises an additional immunostimulant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

Another preferred immunostimulants for use in the present invention is Quil A and its derivatives. Quil A is a saponin preparation isolated from the South American tree *Quilaja Saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina which induces CD8+ cytotoxic T cells (CTLs), Th1 cells and a predominant IgG2a antibody response and is a preferred saponin in the context of the present invention.

Particular formulations of QS21 have been described which are particularly preferred, these formulations further comprise a sterol (WO96/33739). Where squalene and a saponin (optionally QS21) are included, it is of benefit to also include a sterol (optionally cholesterol) to the formulation as this allows a reduction in the total level of oil in the emulsion. This leads to a reduced cost of manufacture, improvement of the overall comfort of the vaccination, and also qualitative and quantitative improvements of the resultant immune responses, such as improved IFN-γ production. Accordingly, the adjuvant system of the present invention typically comprises a ratio of metabolisable oil:saponin (w/w) in the range of 200:1 to 300:1, also the present invention can be used in a "low oil" form the optional range of which is 1:1 to 200:1, optionally 20:1 to 100:1, or substantially 48:1, this vaccine retains the beneficial adjuvant properties of all of the components, with a much reduced reactogenicity profile. Accordingly, some embodiments have a ratio of squalene:QS21 (w/w) in the range of 1:1 to 250:1, or 20:1 to 200:1, or 20:1 to 100:1, or substantially 48:1. Optionally a sterol (e.g. cholesterol) is also included present at a ratio of saponin:sterol as described herein.

Antigens and Antigen Composition

The vaccine or immunogenic formulations will contain an antigen or antigenic composition capable of eliciting an immune response against a human or animal pathogen.

Suitably, said antigen or antigenic composition is derived from one or more of the following: HIV-1, (such as gag or fragments thereof such as p24, tat, nef, gp120 or gp160 or fragments of any of these), human herpes viruses, such as gD or derivatives thereof or Immediate Early protein such as ICP27 from HSV1 or HSV2, cytomegalovirus ((esp Human) (such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F, N, M and G proteins or derivatives thereof), SARS virus, parainfluenza virus, measles virus, mumps virus, human papilloma viruses (for example HPV6, 11, 16, 18), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by R. Gluck, Vaccine, 1992, 10, 915-920) or purified or recombinant proteins thereof, such as HA, NP, NA, or M proteins, or combinations thereof), or derived from bacterial pathogens such as Neisseria spp, including N. gonorrhea and N. meningitidis (for example capsular saccharides and conjugates thereof, transferrin-binding proteins, lactoferrin binding proteins, PilC, adhesins); S. pyogenes (for example M proteins or fragments thereof, C5A protease, lipoteichoic acids), S. agalactiae, S. mutans; H. ducreyi; Moraxella spp, including M catarrhalis, also known as Branhamella catarrhalis (for example high and low molecular weight adhesins and invasins); Bordetella spp, including B. pertussis (for example pertactin, pertussis toxin or derivatives thereof, filamenteous hemagglutinin, adenylate cyclase, fimbriae), B. parapertussis and B. bronchiseptica; Mycobacterium spp., including M. tuberculosis (for example ESAT6, Antigen 85A, -B or -C), M. bovis, M. leprae, M. avium, M. paratuberculosis, M. smegmatis; Legionella spp, including L. pneumophila; Escherichia spp, including enterotoxic E. coli (for example colonization factors, heat-labile toxin or derivatives thereof, heat-stable toxin or derivatives thereof), enterohemorragic E. coli, enteropathogenic E. coli (for example shiga toxin-like toxin or derivatives thereof); Vibrio spp, including V. cholera (for example cholera toxin or derivatives thereof); Shigella spp, including S. sonnei, S. dysenteriae, S. flexnerii; Yersinia spp, including Y. enterocolitica (for example a Yop protein), Y. pestis, Y. pseudotuberculosis; Campylobacter spp, including C. jejuni (for example toxins, adhesins and invasins) and C. coli; Salmonella spp, including S. typhi, S. paratyphi, S. choleraesuis, S. enteritidis; Listeria spp., including L. monocytogenes; Helicobacter spp, including H. pylori (for example urease, catalase, vacuolating toxin); Pseudomonas spp, including P. aeruginosa; Staphylococcus spp., including S. aureus, S. epidermidis; Enterococcus spp., including E. faecalis, E. faecium; Clostridium spp., including C. tetani (for example tetanus toxin and derivative thereof), C. botulinum (for example botulinum toxin and derivative thereof), C. difficile (for example clostridium toxins A or B and derivatives thereof); Bacillus spp., including B. anthracis (for example botulinum toxin and derivatives thereof); Corynebacterium spp., including C. diphtheriae (for example diphtheria toxin and derivatives thereof); Borrelia spp., including B. burgdorferi (for example OspA, OspC, DbpA, DbpB), B. garinii (for example OspA, OspC, DbpA, DbpB), B. afzelii (for example OspA, OspC, DbpA, DbpB), B. andersonii (for example OspA, OspC, DbpA, DbpB), B. hermsii; Ehrlichia spp., including E. equi and the agent of the Human Granulocytic Ehrlichiosis; Rickettsia spp, including R. rickettsii; Chlamydia spp., including C. trachomatis (for example MOMP, heparin-binding proteins), C. pneumoniae (for example MOMP, heparin-binding proteins), C. psittaci; Leptospira spp., including L. interrogans; Treponema spp., including T. pallidum (for example the rare outer membrane proteins), T. denticola, T. hyodysenteriae; or derived from parasites such as Plasmodium spp., including P. falciparum; Toxoplasma spp., including T. gondii (for example SAG2, SAG3, Tg34); Entamoeba spp., including E. histolytica; Babesia spp., including B. microti; Trypanosoma spp., including T. cruzi; Giardia spp., including G. lamblia; Leshmania spp., including L. major; Pneumocystis spp., including P. carinii; Trichomonas spp., including T. vaginalis; Schisostoma spp., including S. mansoni, or derived from yeast such as Candida spp., including C. albicans; Cryptococcus spp., including C. neoformans.

Compositions of the present invention may be used for the prophylaxis or therapy of allergy. Such vaccines would comprise allergen specific and allergen non-specific antigens.

Other preferred specific antigens for M. tuberculosis are for example Tb Ra12, Tb H9, Tb Ra35, Tb38-1, Erd 14, DPV, MTI, MSL, mTTC2 and hTCC1 (WO 99/51748). Proteins for M. tuberculosis also include fusion proteins and variants thereof where at least two, preferably three polypeptides of M. tuberculosis are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI (WO 99/51748).

Most preferred antigens for Chlamydia include for example the High Molecular Weight Protein (HMW) (WO 99/17741), ORF3 (EP 366 412), and putative membrane proteins (Pmps). Other Chlamydia antigens of the vaccine formulation can be selected from the group described in WO 99/28475.

Preferred bacterial vaccines comprise antigens derived from Streptococcus spp, including S. pneumoniae (for example, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other preferred bacterial vaccines comprise antigens derived from Haemophilus spp., including H. influenzae type B, non typeable H. influenzae, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Derivatives of Hepatitis B Surface antigen are well known in the art and include, inter alia, those PreS1, PreS2 S antigens set forth described in European Patent applications EP-A-414 374; EP-A-0304 578, and EP 198-474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise antigen derived from the Human Papilloma Virus (HPV) considered to be responsible for genital warts (HPV 6 or HPV 11 and others), and the HPV viruses responsible for cervical cancer (HPV16, HPV18 and others).

Particularly preferred forms of genital wart prophylactic, or therapeutic, vaccine comprise L1 protein, and fusion proteins comprising one or more antigens selected from the HPV proteins E1, E2, E5, E6, E7, L1, and L2.

The most preferred forms of fusion protein are: L2E7 as disclosed in WO 96/26277, and protein D(1/3)-E7 disclosed in WO99/10375.

A preferred HPV cervical infection or cancer, prophylaxis or therapeutic vaccine, composition may comprise HPV 16 or 18 antigens.

Particularly preferred HPV 16 antigens comprise the early proteins E6 or E7 in fusion with a protein D carrier to form Protein D-E6 or E7 fusions from HPV 16, or combinations thereof; or combinations of E6 or E7 with L2 (WO 96/26277).

Alternatively the HPV 16 or 18 early proteins E6 and E7, may be presented in a single molecule, preferably a Protein D-E6/E7 fusion. Such vaccine may optionally contain either or both E6 and E7 proteins from HPV 18, preferably in the form of a Protein D-E6 or Protein D-E7 fusion protein or Protein D E6/E7 fusion protein.

The vaccine of the present invention may additionally comprise antigens from other HPV strains, preferably from strains HPV 31 or 33.

Vaccines or immunogenic compositions of the present invention further comprise antigens derived from parasites that cause Malaria, for example, antigens from *Plasmodia falciparum* including circumsporozoite protein (CS protein), RTS,S, MSP1, MSP3, LSA1, LSA3, AMA1 and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in International Patent Application No. PCT/EP92/02591, published under Number WO 93/10152 claiming priority from UK patent application No. 9124390.7. When expressed in yeast RTS is produced as a lipoprotein particle, and when it is co-expressed with the S antigen from HBV it produces a mixed particle known as RTS,S. TRAP antigens are described in International Patent Application No. PCT/GB89/00895, published under WO 90/01496. *Plasmodia* antigens that are likely candidates to be components of a multistage Malaria vaccine are *P. falciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in *Plasmodium* spp. One embodiment of the present invention is a malaria vaccine wherein the antigen preparation comprises RTS,S or CS protein or a fragment thereof such as the CS portion of RTS,S, in combination with one or more further malarial antigens, either or both of which may be attached to the Shiga toxin B subunit in accordance with the invention. The one or more further malarial antigens may be selected for example from the group consisting of MPS1, MSP3, AMA1, LSA1 or LSA3.

The formulations may also contain an anti-tumour antigen and be useful for the immunotherapeutic treatment of cancers. For example, the adjuvant formulation finds utility with tumour rejection antigens such as those for prostrate, breast, colorectal, lung, pancreatic, renal or melanoma cancers. Exemplary antigens include MAGE 1 and MAGE 3 or other MAGE antigens (for the treatment of melanoma), PRAME, BAGE, or GAGE (Robbins and Kawakami, 1996, Current Opinions in Immunology 8, pps 628-636; Van den Eynde et al., International Journal of Clinical & Laboratory Research (submitted 1997); Correale et al. (1997), Journal of the National Cancer Institute 89, p 293. Indeed these antigens are expressed in a wide range of tumour types such as melanoma, lung carcinoma, sarcoma and bladder carcinoma. Other tumour-specific antigens are suitable for use with the adjuvants of the present invention and include, but are not restricted to tumour-specific gangliosides, Prostate specific antigen (PSA) or Her-2/neu, KSA (GA733), PAP, mammaglobin, MUC-1, carcinoembryonic antigen (CEA), p501S (prostein). Accordingly in one aspect of the present invention there is provided a vaccine comprising an adjuvant composition according to the invention and a tumour rejection antigen. In one aspect, the tumour antigen is Her-2/neu.

An aspect of the present invention provides that the vaccines comprise a tumour antigen such as prostrate, breast, colorectal, lung, pancreatic, renal, ovarian or melanoma cancers. Accordingly, the formulations may contain tumour-associated antigen, as well as antigens associated with tumour-support mechanisms (e.g. angiogenesis, tumour invasion). Additionally, antigens particularly relevant for vaccines in the therapy of cancer also comprise Prostate-specific membrane antigen (PSMA), Prostate Stem Cell Antigen (PSCA), p501S (prostein), tyrosinase, survivin, NY-ESO1, prostase, PS108 (WO 98/50567), RAGE, LAGE, HAGE. Additionally said antigen may be a self peptide hormone such as whole length Gonadotrophin hormone releasing hormone (GnRH, WO 95/20600), a short 10 amino acid long peptide, useful in the treatment of many cancers, or in immunocastration.

Vaccination

The vaccine preparations containing immunogenic compositions of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). In addition, the vaccines of the invention may be administered IM for priming doses and IN for booster doses.

The content of protein antigens in the vaccine will typically be in the range 1-100 µg, preferably 5-50 µg, most typically in the range 5-25 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines of the present invention may be stored in solution or lyophilized. Preferably the solution is lyophilized in the presence of a sugar such as sucrose or lactose. It is still further preferable that they are lyophilized and extemporaneously reconstituted prior to use.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms a preferred feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of antigens in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are preferably present in as little as 0.1 to 10 µg, preferably 0.1 to 5 µg per dose; and the saccharide (preferably conjugated) antigens may be present in the range of 0.01-1 µg, and preferably between 0.01 to 0.5 µg of saccharide per dose.

As used herein, the term "intradermal delivery" means delivery of the vaccine to the region of the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

The amount of each antigen in each vaccine dose is selected as an amount which induces an immunoprotective response without significant, adverse side effects in typical vaccinees. Such amount will vary depending upon which specific immunogen is employed and how it is presented.

In a further embodiment there is provided a method of treatment of an individual susceptible to or suffering from a disease by the administration of a composition as substantially described herein.

Also provided is a method to prevent an individual from contracting a disease selected from the group comprising infectious bacterial and viral diseases, parasitic diseases, particularly intracellular pathogenic disease, proliferative diseases such as prostate, breast, colorectal, lung, pancreatic, renal, ovarian or melanoma cancers; non-cancer chronic disorders, allergy comprising the administration of a composition as substantially described herein to said individual.

In a further embodiment there is provided a vaccine composition for use in the prophylactic therapy or therapy of a condition or disease wherein the vaccine composition comprises an antigen or antigen composition and an adjuvant composition consisting of an oil in water emulsion comprising 0.5-10 mg metabolisable oil, 0.5-11 mg tocol and 0.1-4 mg emulsifying agent, per human dose.

In a further embodiment there is provided the use of a vaccine composition in the manufacture of a medicament for use in prophylactic therapy or therapy of a condition or disease wherein the vaccine composition comprises an antigen or antigen composition and an adjuvant composition consisting of an oil in water emulsion comprising 0.5-10 mg metabolisable oil, 0.5-11 mg tocol and 0.1-4 mg emulsifying agent, per human dose.

The invention will be further described by reference to the following, non-limiting, examples:

Example I describes immunological read-out methods used in mice, ferrets, pigs and human studies.

Example II describes the preparation of the oil in water emulsion and adjuvant formulations used in the studies exemplified.

Example III shows a clinical trial in an adult population aged 18-59 years with a vaccine containing a split influenza antigen preparation and various doses of AS03 adjuvant Example IV shows a preclinical evaluation of adjuvanted and non-adjuvanted split influenza vaccines (comprising various doses of AS03 adjuvant) in primed BALB/c mice Example V shows a preclinical evaluation of adjuvanted and non-adjuvanted split influenza vaccines (comprising various doses of AS03 adjuvant) in primed C57Bl/6 mice Example VI shows a preclinical evaluation of adjuvanted and non-adjuvanted split influenza vaccines (comprising various doses of AS03 adjuvant and low dose antigen) in primed C57Bl/6 mice Example VII shows a preclinical evaluation of adjuvanted and non-adjuvanted split H5N1 vaccines (comprising various doses of AS03 adjuvant and antigen) in naïve C57Bl/6 mice Example VIII shows a preclinical evaluation of adjuvanted and non-adjuvanted influenza vaccines in primed Large White pigs Example I—Immunological Read-Out Methods I.1. Mice Methods I.1.1. Hemagglutination Inhibition Test Test Principle (Classical Procedure).

Anti-Hemagglutinin antibody titers to the three (seasonal) influenza virus strains are determined using the hemagglutination inhibition test (HI). The principle of the HI test is based on the ability of specific anti-Influenza antibodies to inhibit hemagglutination of red blood cells (RBC) by influenza virus hemagglutinin (HA). Heat inactivated sera are treated by Kaolin and RBC to remove non-specific inhibitors. After pretreatment, two-fold dilutions of sera are incubated with 4 hemagglutination units of each influenza strain. Red blood cells are then added and the inhibition of agglutination is scored. The titers are expressed as the reciprocal of the highest dilution of serum that completely inhibited hemagglutination. As the first dilution of sera is 1:20, an undetectable level is scored as a titer equal to 10.

Adaptation for H5N1 (Specific Description of HI using Horse Erythrocytes):

As the classical HI assay for determining anti-HA antibodies was documented to not well function for the H5N1 strain, and adapted protocol using horse RBC was used. Erythrocytes of horses are used for the H5N1 Pandemic strains. 0.5% (end concentration) horse red blood cell suspension in phosphate buffer containing 0.5% BSA (bovine serum albumin, end concentration). This suspension is prepared every day by washing red blood cell with the same phosphate buffer and a subsequent centrifugation step (10 min, 2000 rpm). This washing step has to be repeated once. After the addition of the horse red blood cells to the reaction mix of sera and virus suspension; the plates have to be incubated at room temperature (RT, 20° C.+/−2° C.) for two hours due to the low sedimentation rate of the horse red blood cells.

Statistical Analysis

Statistical analysis were performed on post vaccination HI titers using UNISTAT. The protocol applied for analysis of variance can be briefly described as follow:

Log transformation of data

Shapiro-Wilk test on each population (group) in order to verify the normality of groups distribution Cochran test in order to verify the homogenicity of variance between the different populations (groups)

Analysis of variance on selected data.

Test for interaction of two-way ANOVA

Tukey-HSD Test for multiple comparisons

I.1.2. Intracellular Cytokine Staining

This technique allows a quantification of antigen specific T lymphocytes on the basis of cytokine production: effector T cells and/or effector-memory T cells produce IFN-γ and/or central memory T cells produce IL-2. PBMCs are harvested at day 7 post-immunization.

Lymphoid Cells are Re-Stimulated in vitro in the Presence of Secretion Inhibitor (Brefeldine). These cells are then processed by conventional immunofluorescent procedure using fluorescent antibodies (CD4, CD8, IFN-γ and IL-2). Results are expressed as a frequency of cytokine positive cell within CD4/CD8 T cells. Intracellular staining of cytokines of T cells was performed on PBMC 7 days after the second immunization. Blood was collected from mice and pooled in heparinated medium RPMI+ Add. For blood, RPMI+Add-diluted PBL suspensions were layered onto a Lympholyte—Mammal gradient according to the recommended protocol (centrifuge 20 min at 2500 rpm and R.T.). The mononuclear cells at the interface were removed, washed 2× in RPMI+Add and PBMCs suspensions were adjusted to $2 \times 10^6$ cells/ml in RPMI 5% fetal calf serum.

In vitro antigen stimulation of PBMCs was carried out at a final concentration of $1 \times 10^7$ cells/ml (tube FACS) with Whole F1 (1 µgHA/strain) and then incubated 2 hrs at 37° C. with the addition of anti-CD28 and anti-CD49d (1 µg/ml for both).

Following the antigen restimulation step, PBMC are incubated overnight at 37° C. in presence of Brefeldin (1 µg/ml) at 37° C. to inhibit cytokine secretion.

IFN-γ/IL-2/CD4/CD8 staining was performed as follows: Cell suspensions were washed, resuspended in 50 µl of PBS 1% FCS containing 2% Fc blocking reagent (1/50; 2.4G2). After 10 min incubation at 4° C., 50 µl of a mixture of anti-CD4-PE (2/50) and anti-CD8 perCp (3/50) was added and incubated 30 min at 4° C. After a washing in PBS 1% FCS, cells were permeabilized by resuspending in 200 µl of Cytofix-Cytoperm (Kit BD) and incubated 20 min at 4° C. Cells were then washed with Perm Wash (Kit BD) and resuspended with 50 µl of a mix of anti-IFN-γ APC (1/50)+ anti-IL-2 FITC (1/50) diluted in Perm Wash. After an incubation min 2 h max overnight at 4° C., cells were washed with Perm Wash and resuspended in PBS 1% FCS+1% paraformaldohyde. Sample analysis was performed by FACS. Live cells were gated (FSC/SSC) and acquisition was performed on ~20,000 events (lymphocytes) or 35,000 events on CD4+ T cells. The percentages of IFN-γ+ or IL2+ were calculated on CD4+ and CD8+ gated populations.

I.1.3. Anti-H5N1 ELISA.

Quantitation of anti-H5N1 Ig, IgG1 and IgG2b antibody titers was performed by ELISA using split H5N1 as coating. Virus and antibody solutions were used at 100 µl per well. Split virus H5N1 was diluted at a final concentration of 1 µg/ml in PBS and was adsorbed overnight at 4° C. to the wells of 96 wells microtiter plates (Maxisorb Immunoplate Nunc 439454). The plates were then incubated for 1 hour at 37° C. with 200 µl per well of PBS containing 1% BSA and 0.1% Tween 20 (saturation buffer). Twelve two-fold dilutions of sera in saturation buffer were added to the H5N1-coated plates and incubated for 1 h 30 at 37° C. The plates were washed four times with PBS 0.1% Tween 20. Biotinilated-conjugated anti-mouse Ig (Prozan-E0413) diluted 1/500 or Biotinilated-conjugated anti-mouse IgG1(Imtech 1070-08), or a biotynilated anti-mouse IgG2b (Imtech 1090-08) dimuated 1/4000 in PBS 1% BSA 0.1% Tween 20 was added to each well and incubated for 1.30 hour at 37° C.; after a washing step, plates were incubated 30 min with a Streptavidine-Biotine-Preoxidase conjugated (Prozan P0397) diluted 1/10000 in PBS 1% BSA Tween 20.

For the colorimetric revelation, plates were incubated 20 min at 22° C. with a solution of o-phenyldiamine (Sigma P4664) 0.04% H2O2 0.03% in 0.1 M citrate buffer pH 4.2. The reaction was stopped with $H_2SO_4$ 2N and microplates were read at 490-630 nm.

I.2. Ferrets Methods

I.2.1. Hemagglutination Inhibition Test (HI)

Test Procedure.

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pre-treatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:10, an undetectable level was scored as a titer equal to 5.

Statistical Analysis.

Statistical analysis were performed on HI titers (Day 41, before challenge) using UNISTAT. The protocol applied for analysis of variance can be briefly described as followed:

Log transformation of data.

Shapiro-wilk test on each population (group) in order to verify the normality of groups distribution.

Cochran test in order to verify the homogenicity of variance between the different populations (groups).

Test for interaction of one-way ANOVA.

Tuckey-HSD Test for multiple comparisons.

I.2.2. Body Temperature Monitoring

Individual temperatures were monitored during the challenge period with the transmitters and by the telemetry recording. All implants were checked and refurbished and a new calibration was performed by DSI (Data Sciences International, Centaurusweg 123, 5015 TC Tilburg, The Netherlands) before placement in the intraperitoneal cavity. All animals were individually housed in single cage during these measurements. Temperatures were recorded every 15 minutes 4 days before challenge until 7 days Post-challenge.

I.2.3. Nasal Washes

The nasal washes were performed by administration of 5 ml of PBS in both nostrils in awoke animals. The inoculum was collected in a Petri dish and placed into sample containers on dry ice.

Viral Titration in Nasal Washes

All nasal samples were first sterile filtered through Spin X filters (Costar) to remove any bacterial contamination. 50 µl of serial ten-fold dilutions of nasal washes were transferred to microtiter plates containing 50 µl of medium (10 wells/dilution). 100 µl of MDCK cells ($2.4 \times 10^5$ cells/ml) were then added to each well and incubated at 35° C. for 5-7 days.

After 5-7 days of incubation, the culture medium is gently removed and 100 µl of a 1/20 WST-1 containing medium is added and incubated for another 18 hrs.

The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD correspond to +/−3 StDev of OD of uninfected control cells). A positive score is defined when OD is <cut-off and in contrast a negative score is defined when OD is >cut-off. Viral shedding titers were determined by "Reed and Muench" and expressed as Log TCID50/ml.

I.3. Pig Methods

I.3.1. Hemagglutination Inhibition Test (HI)

Test Procedure.

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pre-treatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:10, an undetectable level was scored as a titer equal to 5.

Statistical Analysis.

Statistical analysis were performed on HI titers (Day 41, before challenge) using UNISTAT. The protocol applied for analysis of variance can be briefly described as followed:

Log transformation of data.

Shapiro-wilk test on each population (group) in order to verify the normality of groups distribution.

Cochran test in order to verify the homogenicity of variance between the different populations (groups).

Test for interaction of one-way ANOVA.

Tuckey-HSD Test for multiple comparisons.

I.4. Assays for Assessing the Immune Response in Humans

I.4.1. Hemagglutination Inhibition Assay

The immune response was determined by measuring HI antibodies using the method described by the WHO Collaborating Centre for influenza, Centres for Disease Control, Atlanta, USA (1991).

Antibody titre measurements were conducted on thawed frozen serum samples with a standardised and comprehensively validated micromethod using 4 hemagglutination-inhibiting units (4 HIU) of the appropriate antigens and a 0.5% fowl erythrocyte suspension. Non-specific serum inhibitors were removed by heat treatment and receptor-destroying enzyme.

The sera obtained were evaluated for HI antibody levels. Starting with an initial dilution of 1:10, a dilution series (by a factor of 2) was prepared up to an end dilution of 1:20480. The titration end-point was taken as the highest dilution step that showed complete inhibition (100%) of hemagglutination. All assays were performed in duplicate.

I.4.2. Neuraminidase Inhibition Assay

The assay was performed in fetuin-coated microtitre plates. A 2-fold dilution series of the antiserum was prepared and mixed with a standardised amount of influenza A H3N2, H1N1 or influenza B virus. The test was based on the biological activity of the neuraminidase which enzymatically releases neuraminic acid from fetuin. After cleavage of the terminal neuraminic acid β-D-glactose-N-acetyl-galactosamin was unmasked. Horseradish peroxidase (HRP)-labelled peanut agglutinin from Arachis hypogaea, which binds specifically to the galactose structures, was added to the wells. The amount of bound agglutinin can be detected and quantified in a substrate reaction with tetra-methylbenzidine (TMB) The highest antibody dilution that still inhibits the viral neuraminidase activity by at least 50% was indicated is the NI titre.

I.4.3. Neutralising Antibody Assay

Neutralising antibody measurements were conducted on thawed frozen serum samples. Virus neutralisation by antibodies contained in the serum was determined in a microneutralization assay. The sera were used without further treatment in the assay. Each serum was tested in triplicate. A standardised amount of virus was mixed with serial dilutions of serum and incubated to allow binding of the antibodies to the virus. A cell suspension, containing a defined amount of MDCK cells was then added to the mixture of virus and antiserum and incubated at 33° C. After the incubation period, virus replication was visualised by hemagglutination of chicken red blood cells. The 50% neutralisation titre of a serum was calculated by the method of Reed and Muench.

I.4.4. Cell-mediated Immunity was evaluated by Cytokine Flow Cytometry (CFC)

Peripheral blood antigen-specific CD4 and CD8 T cells can be restimulated in vitro to produce IL-2, CD40L, TNF-alpha and IFN if incubated with their corresponding antigen.

Consequently, antigen-specific CD4 and CD8 T cells can be enumerated by flow cytometry following conventional immunofluorescence labelling of cellular phenotype as well as intracellular cytokines production. In the present study, Influenza vaccine antigen as well as peptides derived from specific influenza protein were used as antigen to restimulate Influenza-specific T cells. Results were expressed as a frequency of cytokine(s)-positive CD4 or CD8 T cell within the CD4 or CD8 T cell sub-population.

I.4.5. Statistical Methods

I.4.5.1. Primary Endpoints

Percentage, intensity and relationship to vaccination of solicited local and general signs and symptoms during a 7 day follow-up period (i.e. day of vaccination and 6 subsequent days) after vaccination and overall.

Percentage, intensity and relationship to vaccination of unsolicited local and general signs and symptoms during a 21 day follow-up period (i.e. day of vaccination and 20 subsequent days) after vaccination and overall.

Occurrence of serious adverse events during the entire study.

I.4.5.2. Secondary Endpoints

For the Humoral Immune Response:

Observed Variables:

At days 0 and 21: serum hemagglutination-inhibition (HI) and NI antibody titres, tested separately against each of the three influenza virus strains represented in the vaccine (anti-H1N1, anti-H3N2 & anti-B-antibodies).

At days 0 and 21: neutralising antibody titres, tested separately against each of the three influenza virus strains represented in the vaccine Derived Variables (with 95% Confidence Intervals):

Geometric mean titres (GMTs) of serum HI antibodies with 95% confidence intervals (95% CI) pre and post-vaccination Seroconversion rates* with 95% CI at day 21

Conversion factors** with 95% CI at day 21

Seroprotection rates*** with 95% CI at day 21

Serum NI antibody GMTs' (with 95% confidence intervals) at all timepoints.

*Seroconversion rate defined as the percentage of vaccinees who have at least a 4-fold increase in serum HI titres on day 21 compared to day 0, for each vaccine strain.
**Conversion factor defined as the fold increase in serum HI GMTs on day 21 compared to day 0, for each vaccine strain.
***Protection rate defined as the percentage of vaccinees with a serum HI titre=40 after vaccination (for each vaccine strain) that usually is accepted as indicating protection.

It should be understood, that for some of the clinical trials, reactogenicity/safety may be secondary endpoints, and immunogenicity may be the primary endpoint.

For the Cell Mediated Immune (CMI) Response

Observed Variable

At days 0 and 21: frequency of cytokine-positive CD4/CD8 cells per $10^6$ in different tests.

Each test quantifies the response of CD4/CD8 T cell to:

Peptide Influenza (pf) antigen (the precise nature and origin of these antigens needs to be given/explained Split Influenza (sf) antigen Whole Influenza (wf) antigen.

Derived Variables:

cells producing at least two different cytokines (CD40L, IL-2, IFNγ, TNFα)

cells producing at least CD40L and another cytokine (IL-2, TNFα, IFNγ)

cells producing at least IL-2 and another cytokine (CD40L, TNFα, IFNγ)

cells producing at least IFNγ and another cytokine (IL-2, TNFα, CD40L)

cells producing at least TNFα and another cytokine (IL-2, CD40L, IFNγ)

I.3.5.3. Analysis of Immunogenicity

The immunogenicity analysis was based on the total vaccinated cohort. For each treatment group, the following parameters (with 95% confidence intervals) were calculated:

Geometric mean titres (GMTs) of HI and NI antibody titres at days 0 and 21

Geometric mean titres (GMTs) of neutralising antibody titres at days 0 and 21.

Conversion factors at day 21.

Seroconversion rates (SC) at day 21 defined as the percentage of vaccinees that have at least a 4-fold increase in serum HI titres on day 21 compared to day 0.

Protection rates at day 21 defined as the percentage of vaccinees with a serum HI titre=1:40.

The frequency of CD4/CD8 T-lymphocytes secreting in response was summarised (descriptive statistics) for each vaccination group, at each timepoint (Day 0, Day 21) and for each antigen (Peptide influenza (pf), split influenza (sf) and whole influenza (wf)).

Descriptive statistics in individual difference between timepoint (Post-Pre) responses fore each vaccination group and each antigen (pf, sf, and wf) at each 5 different tests.

A non-parametric test (Kruskall-Wallis test) was used to compare the location differences between the 3 groups and the statistical p-value was calculated for each antigen at each 5 different tests. All significance tests were two-tailed. P-values less than or equal to 0.05 were considered as statistically significant.

Example II—Preparation of the Oil in Water Emulsion and Adjuvant Formulations

Unless otherwise stated, the oil/water emulsion used in the subsequent examples is composed an organic phase made of 2 oils (alpha-tocopherol and squalene), and an aqueous phase of PBS containing Tween 80 as emulsifying agent. Unless otherwise stated, the oil in water emulsion adjuvant formulations used in the subsequent examples were made comprising the following oil in water emulsion component (final concentrations given): 2.5% squalene (v/v), 2.5% alpha-tocopherol (v/v), 0.9% polyoxyethylene sorbitan monooleate (v/v) (Tween 80), see WO 95/17210. This emulsion, termed AS03 in the subsequent examples, was prepared as followed as a two-fold concentrate.

II.1. Preparation of Emulsion SB62

This method was used in the studies reported in the clinical and pre-clinical examples sections. The preparation of the SB62 emulsion is made by mixing under strong agitation of an oil phase composed of hydrophobic components (DL-α-tocopherol and squalene) and an aqueous phase containing the water soluble components (the anionic detergent Tween 80 and PBS mod (modified), pH 6.8). While stirring, the oil phase (1/10 total volume) is transferred to the aqueous phase (9/10 total volume), and the mixture is stirred for 15 minutes at room temperature. The resulting mixture then subjected to shear, impact and cavitation forces in the interaction chamber of a microfluidizer (15000 PSI-8 cycles, or 3 cycles in the adjuvant used in the clinical trial reported in Example III) to produce submicron droplets (distribution between 100 and 200 nm). The resulting pH is between 6.8±0.1. The SB62 emulsion is then sterilised by filtration through a 0.22 μm membrane and the sterile bulk emulsion is stored refrigerated in Cupac containers at 2 to 8° C. Sterile inert gas (nitrogen or argon) is flushed into the dead volume of the SB62 emulsion final bulk container for at least 15 seconds.

The final composition of the SB62 emulsion is as follows:
Tween 80: 1.8% (v/v) 19.4 mg/ml; Squalene: 5% (v/v) 42.8 mg/ml; α-tocopherol: 5% (v/v) 47.5 mg/ml; PBS-mod: NaCl 121 mM, KCl 2.38 mM, Na2HPO4 7.14 mM, KH2PO4 1.3 mM; pH 6.8±0.1.

Example III—Clinical Trial in an Adult Population Aged 18-59 Years with a Vaccine Containing a Split Influenza Antigen Preparation and Various Doses of AS03 Adjuvant (Flu-LD-004)

III.1. Introduction

A phase II, controlled, randomized, single blind study was conducted in an adult population aged 18-59 years old in 2006 in order to evaluate the immunogenicity, safety and reactogenicity of the GlaxoSmithKline Biologicals low dose influenza candidate vaccine (i.e. containing 5 μg HA per strain) with two doses of AS03 adjuvant. The humoral immune response (i.e. anti-hemagglutinin) was measured 21 days after intramuscular administration of one dose of an AS03 adjuvanted vaccine. FLUARIX™ was used as reference.

III.2. Study Design

Three groups of subjects in parallel received the following vaccine intramuscularly:
one group of 100 subjects receiving one injection of the low dose split virus influenza vaccine containing 5 μg HA adjuvanted with AS03 (FluLD1/1)
one group of 100 subjects receiving one injection of the low dose split virus influenza vaccine containing 5 μg HA adjuvanted with a half dose of AS03 (ADO3 ½) (FluLD1/2)
one group of 100 subjects receiving one dose of FLU-ARIX™ (FLUARIX)

Schedule: one IM injection of influenza vaccine at day 0, study site visits at day 0 and day 21 with a blood sample collection (HI antibody determination) and an additional phone contact at day 30 (study conclusion).

The standard trivalent split influenza vaccine—FLU-ARIX™ used in this study, is a commercial vaccine from the year 2006 developed and manufactured by GlaxoSmithKline Biologicals.

III.3. Study Objectives

III.3.1. Primary Objective

To evaluate the humoral immune response induced by the study vaccines in term of anti-haemagglutinin antibody titers:

Observed Variables at Days 0 and 21:
serum Hemagglutination-inhibition antibody titers.
Derived Variables (with 95% Confidence Intervals):
Geometric mean titers (GMTs) of serum antibodies at days 0 and 21
Seroconversion rates* at day 21
Conversion factors** at day 21
Protection rates*** at days 0 and 21

*Seroconversion rate for Haemagglutinin antibody response is defined as the percentage of vaccinees who have either a prevaccination titer <1:10 and a post-vaccination titer 1:40 or a prevaccination titer 1:10 and at least a fourfold increase in post-vaccination titer
**Conversion factor defined as the fold increase in serum HI GMTs post-vaccination compared to day 0;
***Protection rate defined as the percentage of vaccinees with a serum HI titer ≥40 after vaccination that usually is accepted as indicating protection.

III.3.2. Secondary Objective

To evaluate the safety and reactogenicity of the study vaccines in term of solicited local and general adverse events, unsolicited adverse events and serious adverse events:
1. Occurrence, intensity and relationship to vaccination of solicited local and general signs and symptoms during a 7-day follow-up period (i.e. day of vaccination and 6 subsequent days) after each vaccination in each group.
2. Occurrence, intensity and relationship to vaccination of unsolicited local and general signs and symptoms during a 30-day follow-up period (i.e. day of vaccination and 29 subsequent days) after the vaccination in each group.
3. Occurrence and relationship of serious adverse events during the entire study period in each group.

III.4. Vaccine Composition and Administration

III.4.1. Vaccine Preparation

The non-adjuvanted influenza vaccine is a trivalent split virion, inactivated influenza vaccine consisting of three monovalent viral antigen bulks (prepared from respectively influenza strains A/H1N1, A/H3N2 and B). The antigens present in this vaccine are the same as in the licensed FLUARIX™ vaccine which is available on the market as FLUARIX™ (α-Rix®) since 1992 and contain 15 μg HA/strain per dose. The influenza strains included in the FluLD clinical lots are the strains that were chosen for the 2006/2007 Northern Hemisphere:
A/New Caledonia/20/99 (H1N1)-like strain: A/New Caledonia/20/99 (H1N1) IVR-116
A/Wisconsin/67/2005 (H3N2)-like strain: A/Wisconsin/67/2005 (H3N2) NYMCX-161
B/Malaysia/2506/2004.

The antigens are derived from egg-grown viruses. Splitting is carried out with sodium deoxycholate prior to the inactivation step, which is performed through the subsequent action of sodium deoxycholate and formaldehyde.

The AS03 adjuvanted low dose influenza (FluLD) vaccine (clinical lots) is based on the commercially available FLUARIX™ vaccine (prepared from respectively influenza strains A/H1N1, A/H3N2 and B), but with a lower antigen content and adjuvanted with GSK adjuvant system AS03. AS03 consists of an oil-in-water emulsion (SB62) that contains two biodegradable oils, squalene and α-tocopherol (Vitamin E), and a surfactant, polysorbate 80 (Tween 80). Influenza antigens are incorporated in the aqueous phase of the adjuvant system by simple mixing with the emulsion. Two formulations have been tested, differing by the amount of adjuvant introduced with the Flu antigens in the vaccine lot. The adjuvanted vaccines contain 5 μg haemagglutinin (HA) of each influenza virus strain per dose, combined with a full dose (AS03) or half a dose (AS03 ½) of the adjuvant system AS03. The excipients are the following: polysorbate 80 (Tween 80), octoxynol 10 (Triton X-100), alpha-tocopheryl hydrogen succinate, sodium chloride, disodium hydrogen phosphate, potassium dihydrogen phosphate, potassium chloride, water for injection. The AS03 adjuvanted low dose influenza vaccines (FluLD, full or half dose of AS03) are preservative-free vaccines. However, they contain trace amounts of thiomersal (<1.25 μg of Hg per dose) from the early stages of the manufacturing process. They are both presented as monodose vaccines in glass (Type I) pre-filled syringes at a volume of 0.5 ml/dose.

III.4.1.1. Composition of AS03 Adjuvanted Influenza Vaccine

One dose of FluLD (full or half dose of AS03) corresponds to 0.5 ml. The composition is provided in Table 3. The HA content per dose is 5 μg for both formulations, the sole difference being the amount of AS03 present in the final containers.

TABLE 3

Composition of AS03 adjuvanted low dose influenza vaccine (full and half dose of AS03)

| Component | Quantity per dose (0.5 ml) |
|---|---|
| Inactivated split virions | |
| A/New Caledonia/20/99 (H1N1) IVR-116 | 5 μg HA |
| A/Wisconsin/67/2005 (H3N2) NYMCX-161 | 5 μg HA |
| B/Malaysia/2506/2004 | 5 μg HA |
| Adjuvant (Full Dose/HalfDose) | |
| SB62 emulsion (Total Volume) | 0.250 mL |
| squalene | 10.70 mg/5.35 mg |
| DL-α-tocopherol | 11.88 mg/5.94 mg |
| Polysorbate 80 (Tween 80) | 4.85 mg/2.425 mg |
| Polysorbate 80 (Tween 80) | 0.122 mg |
| Octoxynol 10 (Triton X-100) | 0.0283 mg |
| αTocopheryl hydrogen succinate | 0.01665 mg |
| Sodium chloride | 4 mg |
| Disodium phosphate | 0.575 mg |
| Potassium dihydrogen phosphate | 0.100 mg |
| Potassium chloride | 0.101 mg |
| Water for injection | ad 0.50 ml |

Abbreviations:
HA = Haemagglutinin.
The total content in Polysorbate 80 corresponds to 4.972 mg per dose when AS03 full dose is used, and 2.547 mg per dose when AS03 half dose is used.

III.4.1.2. Production of Split Inactivated Influenza Antigen Preparation

The influenza antigens are identical to those included in FLUARIX™ (Influenza Virus Vaccine). The monovalent bulks consist of purified inactivated split viruses that are prepared from working seeds of the three strains of influenza virus, type A (H1N1 and H3N2) and type B, which are grown individually in embryonated hens' eggs. These working seeds are derived from strains that are received from a WHO collaborating center following the annual WHO recommendations. For the process for preparing the antigens reference is, by way of illustration, given to WO 02/097072. The volumes of the three monovalent bulks are based on the HA content measured in each monovalent bulk prior to the formulation and on the target manufacturing volume.

A 10-times concentrated phosphate buffered saline (pH 7.4 when 1 time concentrated) and a pre-mixture of Tween 80 and α-tocopheryl hydrogen succinate are diluted in water for injection, followed by stirring during 5-30 minutes at room temperature.

The three concentrated monovalent bulks are then successively diluted in the resulting phosphate buffered saline/Tween 80-α-tocopheryl hydrogen succinate solution to a concentration of
20 μg HA of each A monovalent bulk (H1N1, H3N2)
23.32 μg HA of B monovalent bulk
per mL of intermediate trivalent bulk (5 μg HA of each A monovalent bulk and 5.83 μg HA of B/500 μl trivalent final bulk).

Between the additions of each monovalent bulk, the mixture is stirred for 10-30 minutes at room temperature and for 15-30 minutes after addition of the last monovalent bulk. This intermediate trivalent bulk also referred to as "prepool" can be held at +2-+8° C. or further processed to the final formulation step on the same day. The final volume of pre-pool is 250 μl per dose.

III.4.1.3. Preparation of the Vaccine Compositions with AS03 Adjuvant

Adjuvanted Vaccine: LD AS03 1/1 (Table 4)

PBS mod 10 fold concentrated (pH 7.4 when one fold concentrated; 137 mM NaCl, 2.7 mM KCl, 8.1 mM Na$_2$HPO$_4$, 1.47 mM KH$_2$PO$_4$, pH 7.4) as well as a mixture containing Tween80, Triton X-100 and VES (quantities taking into account the detergent present in the strains) are added to water for injection. After 5 to 30 minutes stirring, 20 μg HA per ml of each strain H1N1 and H3N2 and 23.32 μg HA per ml of B strain are added with 10 to 30 minutes stirring between each addition. After 15 to 30 minutes stirring, a small volume of the so called "intermediate bulk" are discarded for analysis and stored between +2 and +8° C. The intermediate bulk is in PBS mod 1 fold concentrated. The target's detergents concentration are 488 μg Tween 80 per ml, 73.6 μg Triton X-100 per ml and 66.6 μg VES per ml.

The final formulation is then prepared: an equal volume of SB62 (see preparation in Example II) is added to each 250 μl of pre-pool intermediate bulk and mixed during 30 to 60 minutes at room temperature. pH is checked to range between 6.8 and 7.5. Formulation is flushed with nitrogen and then stored between +2 and 8° C. prior to filling.

TABLE 4

| AS03 adjuvanted low dose vaccine | | |
|---|---|---|
| Component | Concentration | Volume (ml) |
| Step 1: Prepool | | |
| A/New Caledonia monovalent bulk | 104 μg/ml | 302.88 |
| A/Wisconsin monovalent bulk | 85 μg/ml | 370.59 |
| B/Malaysia monovalent bulk | 110 μg/ml | 333.90 |
| PBS mod(1) | See legend | 56.76 |
| Tween 80 | 48000 μg/ml | 5.24 |
| Triton X-100 | | Residual from H3N2 strain |
| α-tocopheryl hydrogen succinate | 26480 μg/ml | 1.2 |
| Filtrated water | | 504.43 |
| | Total volume = | 1575 (ml) |
| | 75 ml of prepool samples are retrieved for testing | |
| | Remaining prepool volume = | 1500 (ml) |
| Step 2: added to prepool | | |
| Emulsion SB62 | | 1500 |
| | Total volume of final bulk = | 3000 (ml) |

(1)The buffer final bulk composition is: 137 mM NaCl, 2.7 mM KCl, 8.1 mM Na$_2$HPO$_4$, 1.47 mM KH$_2$PO$_4$, pH 7.4

Adjuvanted vaccine: LD AS03 ½ (Table 5a)

PBS mod 10 fold concentrated (pH 7.4 when one fold concentrated—see composition above) as well as a mixture containing Tween 80, Triton X-100 and VES (quantities taking into account the detergent present in the strains) are added to water for injection. After 5 to 30 minutes stirring, 20 µg HA per ml of each strain H1N1 and H3N2 and 23.32 µg HA per ml of B strain are added with 10 to 30 minutes stirring between each addition. After 15 to 30 minutes stirring, a small volume of the so called "intermediate bulk" are discarded for analysis and stored between +2 and +8° C. PBS mod is 1 fold concentrated in the intermediate bulk. The target's detergents concentration are 488 µg Tween 80 per ml, 73.6 µg Triton X-100 per ml and 66.6 µg VES per ml Final formulation is then prepared: SB62 is first diluted with the PBS mod buffer and stirred for 15-30 minutes at RT. An equal volume of this diluted SB62 is then added to each 250 µl of pre-pool of intermediate bulk. After 30 to 60 minutes stirring at RT, pH is checked to range between 6.8 and 7.5. Formulation is flushed with nitrogen and then stored between +2 and 8° C. prior to filling.

The final volume of both formulation is 500 µl per dose and the final HA concentration is 10 µg of each A monovalent bulk and 11.66 µg of B monovalent bulk per ml of trivalent final bulk. Final Tween 80, Triton X-100 (residual from H3N2 monobulk manufacturing) and α-tocopheryl hydrogen succinate (α-tocopheryl hydrogen succinate is an ester form of RRR (D isomer)-α-tocopherol) target concentrations are 244 µg/ml, 58.6 µg/ml and 33.3 µg/ml, respectively.

TABLE 5a

AS03 adjuvanted low dose vaccine (half-dose of adjuvant)

| Component | Concentration | Volume (ml) |
|---|---|---|
| Step 1: Prepool | | |
| Step 1: Prepool | | |
| A/New Caledonia monovalent bulk | 104 µg/ml | 300.96 |
| A/Wisconsin monovalent bulk | 85 µg/ml | 368.24 |
| B/Malaysia monovalent bulk | 110 µg/ml | 331.78 |
| PBS mod(1) | See legend | 56.4 |
| Tween 80 | 48000 µg/ml | 5.2 |
| Triton X-100 | | Residual from H3N2 strain |
| α-tocopheryl hydrogen succinate | 26480 µg/ml | 1.2 |
| Filtrated water | | 501.22 |
| | Total volume = | 1565 (ml) |
| | 65 ml of prepool samples are retrieved for testing | |
| Remaining prepool volume = 1500 (ml) | | |
| Step 2: added to prepool | | |
| Emulsion SB62 | | 750 |
| PBS mod(1) | See legend | 75 |

TABLE 5a-continued

AS03 adjuvanted low dose vaccine (half-dose of adjuvant)

| Component | Concentration | Volume (ml) |
|---|---|---|
| Filtrated water | | 675 |
| | Total volume of final bulk = 3000 (ml) | |

(1)The buffer final bulk composition is: 137 mM NaCl, 2.7 mM KCl, 8.1 mM $Na_2HPO_4$, 1.47 mM $KH_2PO_4$, pH 7.4

III.4.2. Vaccine Administration

The vaccine is filled into 1.25-ml sterile Type I (Ph. Eur.) glass syringes. Each syringe is filled to a target of 0.57 ml (range: 0.54-0.60 ml). The vaccines were administered intramuscularly in the deltoid region of the non-dominant arm. All vaccines were presented as pre-filled syringes (0.5 ml). In order to ensure proper IM injection of the vaccine, a needle of at least 25G and at least 2.5 cm in length was used.

III.5 Study Population Results

A total of 300 subjects were enrolled in this study: 100 subjects in each of the 3 groups. The mean age of the total vaccinated cohort at the time of vaccination was 36.7 years with a standard deviation of 13.67 years. The mean age and gender distribution of the subjects across the 3 vaccine groups was similar.

III.6 Immunogenicity Results

Analysis of immunogenicity was performed on the ATP cohort for immunogenicity (297 subjects).

Humoral immune Response

In order to evaluate the humoral immune response induced by the low dose influenza candidate vaccine adjuvanted with AS03, the following parameters (with 95% confidence intervals) were calculated for each treatment group:

- Geometric mean titres (GMTs) of HI antibody titres at days 0 and 21;
- Seroconversion rates (SC) at days 21;
- Conversion factors at day 21;
- Protection rates at day 0 and 21.

III.6.1 HI Geometric Mean Titres (GMT)

The GMTs for HI antibodies with 95% Cl are shown in Table 5b and FIG. 1. Adjusted GMT ratios between groups are shown in Table 5c.

Pre-vaccination GMTs of HI antibodies for all 3 vaccine strains were within the same range in the 3 treatment groups. The observed GMTs at day 21 for adjuvanted groups tends to be higher than FLUARIX™ influenza virus vaccine group for all 3 strains with a statistical difference (no overlapping of 95% CIs and adjusted GMT ratio did not contain the value 1) between FluLD1/1 and FLUARIX™ influenza virus vaccine for the A/Wisconsin vaccine strain. A statistical difference (adjusted GMT ratio did not contain the value 1) was observed also between FluLD1/2 and FLUARIX™ influenza virus vaccine for the B/Malaysia vaccine strain.

TABLE 5b

Seropositivity rates and Geometric mean titers (GMTs) for anti-HA antibody at day 0 and 21 (ATP cohort for immunogenicity)

| | | | | | ≥10 1/DIL | | | GMT | | | | |
|---|---|---|---|---|---|---|---|---|---|---|---|---|
| | | | | | | 95% CI | | | 95% CI | | | |
| Antibody | Group | Timing | N | n | % | LL | UL | 1/DL | LL | UL | Min | Max |
| A/New Caledonia | FluLD1/1 | PRE | 99 | 80 | 80.8 | 71.7 | 88.0 | 31.9 | 23.5 | 43.4 | <10.0 | 2560.0 |
| | | PI(D21) | 99 | 99 | 100 | 96.3 | 100 | 475.4 | 352.2 | 641.6 | 20.0 | 7240.0 |
| | FluLD1/2 | PRE | 99 | 80 | 80.8 | 71.7 | 88.0 | 36.1 | 26.9 | 48.5 | <10.0 | 3620.0 |
| | | PI(D21) | 99 | 98 | 99.0 | 94.5 | 100 | 399.0 | 294.7 | 540.2 | <10.0 | 7240.0 |

TABLE 5b-continued

Seropositivity rates and Geometric mean titers (GMTs) for anti-HA antibody at day 0 and 21 (ATP cohort for immunogenicity)

| Antibody | Group | Timing | N | ≥10 1/DIL | | | | GMT | | | | |
|---|---|---|---|---|---|---|---|---|---|---|---|---|
| | | | | n | % | 95% CI LL | 95% CI UL | 1/DL | 95% CI LL | 95% CI UL | Min | Max |
| | Fluarix | PRE | 98 | 85 | 86.7 | 78.4 | 92.7 | 26.1 | 20.5 | 33.2 | <10.0 | 1280.0 |
| | | PI(D21) | 98 | 98 | 100 | 96.3 | 100 | 380.6 | 274.2 | 528.4 | 10.0 | 7240.0 |
| A/Wisconsin | FluLD1/1 | PRE | 99 | 61 | 61.6 | 51.3 | 71.2 | 16.8 | 13.1 | 21.5 | <10.0 | 453.0 |
| | | PI(D21) | 99 | 99 | 100 | 96.3 | 100 | 276.2 | 223.5 | 341.3 | 28.0 | 5120.0 |
| | FluLD1/2 | PRE | 99 | 66 | 66.7 | 56.5 | 75.8 | 19.9 | 15.2 | 25.9 | <10.0 | 640.0 |
| | | PI(D21) | 99 | 99 | 100 | 96.3 | 100 | 241.9 | 192.9 | 303.4 | 20.0 | 5120.0 |
| | Fluarix | PRE | 98 | 58 | 59.2 | 48.8 | 69.0 | 14.7 | 11.6 | 18.6 | <10.0 | 320.0 |
| | | PI(D21) | 98 | 97 | 99.0 | 94.4 | 100 | 172.3 | 136.4 | 217.6 | <10.0 | 5120.0 |
| B/Malaysia | FluLD1/1 | PRE | 99 | 72 | 72.7 | 62.9 | 81.2 | 20.4 | 15.9 | 26.1 | <10.0 | 453.0 |
| | | PI(D21) | 99 | 99 | 100 | 96.3 | 100 | 268.6 | 221.3 | 326.0 | 28.0 | 2560.0 |
| | FluLD1/2 | PRE | 99 | 76 | 76.8 | 67.2 | 84.7 | 22.2 | 17.6 | 27.9 | <10.0 | 320.0 |
| | | PI(D21) | 99 | 99 | 100 | 96.3 | 100 | 301.5 | 246.1 | 369.4 | 28.0 | 3620.0 |
| | Fluarix | PRE | 98 | 76 | 77.6 | 68.0 | 85.4 | 26.5 | 20.9 | 33.6 | <10.0 | 320.0 |
| | | PI(D21) | 98 | 97 | 99.0 | 94.4 | 100 | 219.2 | 171.4 | 280.2 | <10.0 | 5120.0 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
FLUARIX = FLUARIX ™ influenza virus vaccine vaccine
GMT = Geometric Mean antibody Titer
N = Number of subjects with available results
n/% = number/percentage of seropositive subjects (HI titer >= 1:10)
95% CI = 95% confidence interval, LL = Lower Limit, UL = Upper Limit
MIN/MAX = Minimum/Maximum
PRE = Pre-vaccination at day 0
PI (D21) = Post-vaccination at Day 21

TABLE 5c

Adjusted GMT ratios between groups for each vaccine strain at day 21 (ATP cohort for immunogenicity)

| Antibody | Group description | N | Adjusted GMT | Group description | N | Adjusted GMT | Ratio order | Adjusted GMT ratio Value | 95% CI LL | 95% CI UL |
|---|---|---|---|---|---|---|---|---|---|---|
| A/New Caledonia (1/DIL) | FluLD1/1 | 99 | 472.4 | FluLD1/2 | 99 | 385.0 | FluLD1/1/FluLD1/2 | 1.23 | 0.80 | 1.88 |
| | FluLD1/1 | 99 | 472.3 | Fluarix | 98 | 396.9 | FluLD1/1/Fluarix | 1.19 | 0.78 | 1.82 |
| | FluLD1/2 | 99 | 385.0 | Fluarix | 98 | 397.0 | FluLD1/2/Fluarix | 0.97 | 0.63 | 1.49 |
| A/Wisconsin (1/DIL) | FluLD1/1 | 99 | 277.3 | FluLD1/2 | 99 | 230.0 | FluLD1/1/FluLD1/2 | 1.21 | 0.90 | 1.62 |
| | FluLD1/1 | 99 | 277.5 | Fluarix | 98 | 180.8 | FluLD1/1/Fluarix | 1.54 | 1.14 | 2.06 |
| | FluLD1/2 | 99 | 230.0 | Fluarix | 98 | 180.6 | FluLD1/2/Fluarix | 1.27 | 0.95 | 1.71 |
| B/Malaysia (1/DIL) | FluLD1/1 | 99 | 275.1 | FluLD1/2 | 99 | 303.4 | FluLD1/1/FluLD1/2 | 0.91 | 0.68 | 1.22 |
| | FluLD1/1 | 99 | 275.2 | Fluarix | 98 | 212.7 | FluLD1/1/Fluarix | 1.29 | 0.96 | 1.74 |
| | FluLD1/2 | 99 | 303.4 | Fluarix | 98 | 212.6 | FluLD1/2/Fluarix | 1.43 | 1.06 | 1.92 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
FLUARIX = FLUARIX TM influenza virus vaccine
Adjusted GMT = geometric mean antibody titre adjusted for baseline titre
N = Number of subjects with both pre- and post-vaccination results available
95% CI = 95% confidence interval for the adjusted GMT ratio (Ancova model: adjustment for baseline titre-pooled variance with more than 2 groups);
LL = lower limit, UL = upper limit III.6.2 Conversion Factors of Anti-HI Antibody titres, Seroprotection Rates and Seroconversion Rates (Correlates for Protection as Established for Influenza Vaccine in Humans)

Results are presented in Table 6—FIG. 2 for seroprotection rates, Table 7—FIG. 3 for seroconversion rates and Table 8—FIG. 4 for conversion factors.

The threshold required by the European Authorities for the seroprotection rates (70%) was reached in all groups (at least 94.9%). For each vaccine strain, the seroprotection rates at day 21 for the 3 groups were within the same range.

The threshold required by the European Authorities for the seroconversion rates (40%) was reached in all groups (at least 65%).

For the A/New Caledonia vaccine strain, the SCR at day 21 for the 3 groups were within the same range.

For the A/Wisconsin vaccine strain, the SCR at day 21 for the FluLD1/1 group tended to be higher compared to the FLUARIX™ influenza virus vaccine group. The SCR at day 21 for the FluLD1/2 group was within the same range compared to the FLUARIX™ influenza virus vaccine group.

For the B/Malaysia vaccine strain, the SCR at day 21 for the FluLD1/2 group tended to be higher compared to the FLUARIX™ influenza virus vaccine group. The SCR at day 21 for the FluLD1/1 group was within the same range compared to the FLUARIX™ influenza virus vaccine group.

The threshold required by the European Authorities for the seroconversion factors (2.5) was reached in all groups (at least 6.2).

For the A/New Caledonia vaccine strain, the SCF at day 21 for the 3 groups seemed to be within the same range. The observed value for FluLD1/2 group was lower than the observed value for the FLUARIX™ influenza virus vaccine group but could be explained by the higher pre-vaccination seroprotection rate in the FluLD1/2 group.

For the A/Wisconsin vaccine strain, the SCF at day 21 for the FluLD1/1 group tended to be higher compared to the FLUARIX™ influenza virus vaccine group. The SCF at day 21 for the FluLD1/2 group was within the same range compared to FLUARIX™ influenza virus vaccine group.

For the B/Malaysia vaccine strain, the SCF at day 21 for the two adjuvanted groups tended to be higher compared to the FLUARIX™ influenza virus vaccine group.

TABLE 6

Seroprotection rates (SPR) for HI antibody titer at day 0 and day 21 (ATP cohort for immunogenicity)

| Vaccine strain | Group | Timing | N | n | % | 95% CI LL | 95% CI UL |
|---|---|---|---|---|---|---|---|
| A/New Caledonia | FluLD1/1 | PRE | 99 | 41 | 41.4 | 31.6 | 51.8 |
| | | PI(D21) | 99 | 95 | 96.0 | 90.0 | 98.9 |
| | FluLD1/2 | PRE | 99 | 55 | 55.6 | 45.2 | 65.5 |
| | | PI(D21) | 99 | 97 | 98.0 | 92.9 | 99.8 |
| | Fluarix | PRE | 98 | 35 | 35.7 | 26.3 | 46.0 |
| | | PI(D21) | 98 | 93 | 94.9 | 88.5 | 98.3 |
| A/Wisconsin | FluLD1/1 | PRE | 99 | 32 | 32.3 | 23.3 | 42.5 |
| | | PI(D21) | 99 | 97 | 98.0 | 92.9 | 99.8 |
| | FluLD1/2 | PRE | 99 | 37 | 37.4 | 27.9 | 47.7 |
| | | PI(D21) | 99 | 97 | 98.0 | 92.9 | 99.8 |
| | Fluarix | PRE | 98 | 25 | 25.5 | 17.2* | 35.3* |
| | | PI(D21) | 98 | 93 | 94.9 | 8.5 | |
| B/Malaysia | FluLD1/1 | PRE | 99 | 31 | 31.3 | 22.4 | 41.4 |
| | | PI(D21) | 99 | 97 | 98.0 | 92.9 | 99.8 |
| | FluLD1/2 | PRE | 99 | 39 | 39.4 | 29.7 | 49.7 |
| | | PI(D21) | 99 | 98 | 99.0 | 94.5 | 100 |
| | Fluarix | PRE | 98 | 44 | 44.9 | 34.8 | 55.3 |
| | | PI(D21) | 98 | 94 | 95.9 | 89.9 | 98.9 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
FLUARIX = FLUARIX ™ influenza virus vaccine
N = Number of subjects with available results
n/% = Number/percentage of seroprotected subjects (HI titer >= 40 1/DIL)
95% CI = 95% confidence interval, LL = Lower Limit, UL = Upper Limit
PRE = Pre-vaccination at day 0
PI (D1) = Post-vaccination at Day 21
Data source = Appendix table IIIA

TABLE 7

Seroconversion rate (SCR) for HI antibody titer at day 21 (ATP cohort for immunogenicity)

| Vaccine strain | Group | N | n | % | 95% CI LL | 95% CI UL |
|---|---|---|---|---|---|---|
| A/New Caledonia | FluLD1/1 | 99 | 69 | 69.7 | 59.6 | 78.5 |
| | FluLD1/2 | 99 | 64 | 64.6 | 54.4 | 74.0 |
| | Fluarix | 98 | 66 | 67.3 | 57.1 | 76.5 |
| A/Wisconsin | FluLD1/1 | 99 | 88 | 88.9 | 81.0 | 94.3 |
| | FluLD1/2 | 99 | 79 | 79.8 | 70.5 | 87.2 |
| | Fluarix | 98 | 73 | 74.5 | 64.7 | 82.8 |
| B/Malaysia | FluLD1/1 | 99 | 76 | 76.8 | 67.2 | 84.7 |
| | FluLD1/2 | 99 | 82 | 82.8 | 73.9 | 89.7 |
| | Fluarix | 98 | 65 | 66.3 | 56.1 | 75.6 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
FLUARIX = FLUARIX ™ influenza virus vaccine
Seroconversion defined as: For initially seronegative subjects, antibody titre >=40 1/DIL after vaccination For initially seropositive subjects, antibody titre after vaccination >=4 fold the pre-vaccination antibody titre
N = Number of subjects with pre- and post-vaccination results available
n/% = Number/percentage of seroconverted subjects
95% CI = 95% confidence interval, LL = Lower Limit, UL = Upper Limit

TABLE 8

Seroconversion factor (SCF) for HI antibody titer at day 21 (ATP cohort for immunogenicity)

| Vaccine strain | Group | N | Value | 95% CI LL | 95% CI UL |
|---|---|---|---|---|---|
| A/New Caledonia | FluLD1/1 | 99 | 14.9 | 10.4 | 21.3 |
| | FluLD1/2 | 99 | 11.0 | 7.7 | 15.9 |
| | Fluarix | 98 | 14.6 | 9.9 | 21.6 |
| A/Wisconsin | FluLD1/1 | 99 | 16.5 | 13.0 | 20.9 |
| | FluLD1/2 | 99 | 12.2 | 9.2 | 16.1 |
| | Fluarix | 98 | 11.7 | 8.8 | * |
| B/Malaysia | FluLD1/1 | 99 | 13.2 | 10.0 | 17.4 |
| | FluLD1/2 | 99 | 13.6 | 10.2 | 18.0 |
| | Fluarix | 98 | 8.3 | 6.2 | 11.0 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
FLUARIX = FLUARIX ™ influenza virus vaccine
N = Number of subjects with pre- and post-vaccination results available
SCF = Seroconversion Factor or geometric mean ratio (mean[log10(PI(D21)/PRE)])
95% CI = 95% confidence interval,
LL = Lower Limit,
UL = Upper Limit III.7 Safety Conclusions A higher reactogenicity in terms of solicited (local/general) and unsolicited symptoms in the adjuvanted vaccine groups compared to the FLUARIX™ influenza virus vaccine Group was the global trend observed in this study.

A reduction of the AS03 content in the adjuvanted vaccine has a significant impact on all the general and on the local grade 3 symptoms.

The occurrence of unsolicited symptoms tended to be higher in the adjuvanted vaccine groups (55% and 47% of subjects), compared to the FLUARIX™ influenza virus vaccine Group (35%).

From these results, it can be concluded that the reactogenicity and safety profile of the candidate vaccines is satisfactory and clinically acceptable.

III.8. Overall Conclusions

III.8.1. Immunogenicity Results

The primary objective of this study was to assess humoral immune response (anti-HI antibody titres) elicited by low dose influenza vaccine with two different concentrations of AS03 adjuvant, and by FLUARIX™ influenza virus vaccine.

At Day 21, the three vaccines exceeded the requirements of the European authorities for annual registration of split virion influenza vaccines ("Note for Guidance on Harmonisation of Requirements for influenza Vaccines" for the immuno-logical assessment of the annual strain changes—CPMP/BWP/214/96). GMTs tended to be higher in the adjuvanted groups compared to the FLUARIX™ influenza virus vaccine Group, with a statistically significant difference observed for the A/Wisconsin (FluLD1/1 vs. FLUARIX™ influenza virus vaccine) and B/Malaysia vaccine strains (FluLD1/2 vs. FLUARIX™ influenza virus vaccine). Similar seroprotection rates were observed in all three vaccine groups, ranging from 94.9% to 99%. Seroconversion rates and seroconversion factors were observed to be higher in the adjuvanted groups than in the FLUARIX™ influenza virus vaccine Group. Data from this trial also revealed that the immunogenicity induced by the vaccine with half the dosage of AS03 adjuvant was comparable to that induced with the full dose of adjuvant.

III.8.2. Reactogenicity and Safety Results

The administration of the low dose influenza candidate vaccine adjuvanted with AS03 was safe and clinically well tolerated in the study population, i.e. adult people aged between 18 and 59 years. The half dose adjuvanted vaccine showed a marked decrease in the incidence of solicited local and general symptoms, compared to the full dose adjuvanted vaccine.

Example IV—Preclinical Evaluation of Adjuvanted and Non-Adjuvanted Split Influenza Vaccines (Comprising Various Doses of AS03 Adjuvant) in Primed BALB/c Mice IV.1. Experimental Design and Objective Experiments in influenza-primed mice were performed in order to evaluate the increase in humoral responses by AS03 induced by influenza vaccines formulated with this oil-in-water adjuvant. To simulate the human situation, an experiment was conducted using mice primed with heterosubtypic strains.

IV.1.1. Treatment/Group (Table 9)

Groups of 27 adult female BALB/c mice were primed intranasally (20 µl volume) on day 0 with trivalent whole, formalin-inactivated influenza virus (5 µg HA for each strain). Priming strains consisted of earlier drift variants (5 µg HA whole inactivated H1N1 A/Johannesburg/82/96, H3N2 A/Sydney/5/97, B/Harbin/7/94) to those included in the vaccine. Twenty-eight days later, the mice were vaccinated with a single dose of the vaccine candidate intramuscularly in a total volume of 50 µl. Mice were immunized with formulations containing split antigens alone (trivalent split plain) or formulations containing split antigens adjuvanted with two doses of AS03 (full or ⅕). The strains used for the immunizations included H1N1 A/New Caledonia/20/99, H3N2 A/Panama/2007/99, B/Shangdong/7/97 viral antigens (1.5 µg/strain, $\frac{1}{10}^{th}$ of the human dose).

TABLE 9

| Gr | Antigen/Formulation | Other treatment |
|---|---|---|
| 1 | Trivalent split/Plain (non-adjuvanted) | Heterologous priming D0 |
| 2 | Trivalent split/AS03 | Heterologous priming D0 |
| 3 | Trivalent split/AS03 1/5 | Heterologous priming D0 |

IV.1.2. Preparation of the Vaccine Formulations

A Premix of Tween 80, Triton X100 and Vitamin E Succinate (VES) is prepared in order to reach a final concentration into the vaccine of 750 µg/ml of Tween 80, 110 µg/ml of Triton X100 and 100 µg/ml of VES. The quantities used in the premix are calculated taking into account the quantities of detergent and VES already present in the strains. Preparation of one liter of 10 fold concentrated Saline buffer (PBS pH 7.4): to 0.800 l of water for injection, add NaCl 80 g, KCl 2 g, Na$_2$HPO$_4$ 11.44 g, KH$_2$PO$_4$ 2 g. After solubilization, adjust to 1.0 L with water for injection. pH will be at 7.4 when 10 fold diluted.

Trivalent Split/Plain

The formulation of one 50 µl dose is prepared extemporaneously according the following sequence: Water For Injection+Saline Buffer (10 fold concentrated PBS pH 7.4)+Premix, 5 min magnetic stirring at room temperature, +1.5 µg HA H1N1 strain, 10 min magnetic stirring at room temperature, +1.5 µg HA H3N2 strain, 10 min magnetic stirring at room temperature, +1.5 µg HA B strain, 15 min magnetic stirring at room temperature. The formulations are injected within the hour following the end of their preparation.

Trivalent Split/AS03

A Premix of Tween 80, Triton X100 and Vitamin E Succinate (VES) is prepared in order to reach a final concentration into the vaccine of 750 µg/ml of Tween 80, 110 µg/ml of Triton X100 and 100 µg/ml of VES. The quantities used in the premix are calculated taking into account the quantities of detergent and VES already present in the strains.

The formulation of one 50 µl dose is prepared extemporaneously according the following sequence: Water For Injection+Saline Buffer (10 fold concentrated PBS pH 7.4)+Premix, 5 min magnetic stirring at room temperature, +1.5 µg HA H1N1 strain, 10 min magnetic stirring at room temperature, +1.5 µg HA H3N2 strain, 10 min magnetic stirring at room temperature, +1.5 µgHA B strain, 15 min magnetic stirring at room temperature, +25 µl SB62 emulsion for the full dose AS03 or 5 µl SB62 emulsion for the 1/5 dose AS03, 15 min magnetic stirring at room temperature. The formulations are injected within the hour following the end of their preparation.

IV.1.3. Read-Outs (Table 10)

The humoral immune response to vaccination was measured before immunization (day 28) and 14 days after immunization (27 mice/group). Serum samples were tested by the hemagglutination inhibition (HI) test.

TABLE 10

| Read-out | Timepoint | Sample type | Analysis method |
|---|---|---|---|
| Humoral response | D28, D42 | Sera | IHA |

IV.2. Results

IV.2.1. Humoral Immunity

Figure 5B:
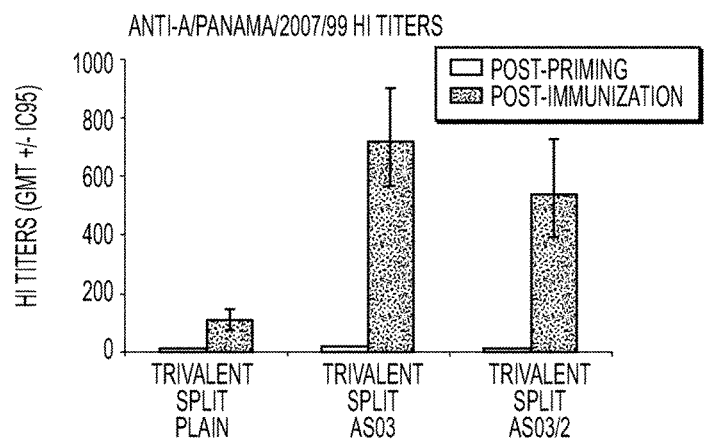
Figure 5C:
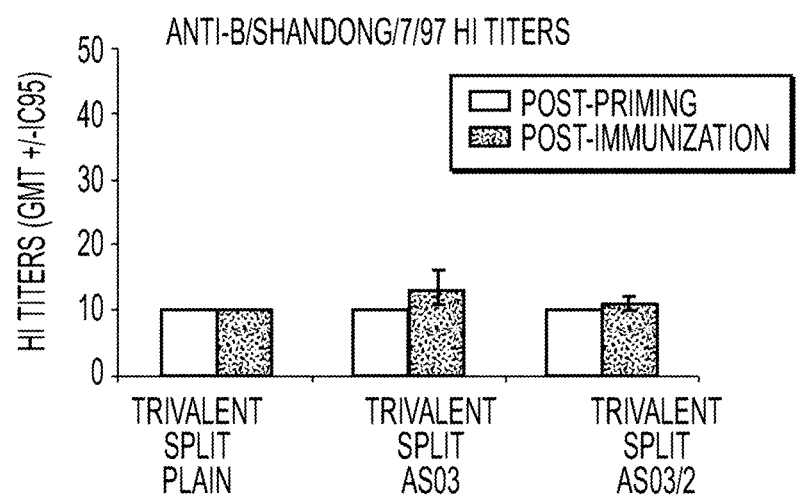
Figure 9C:
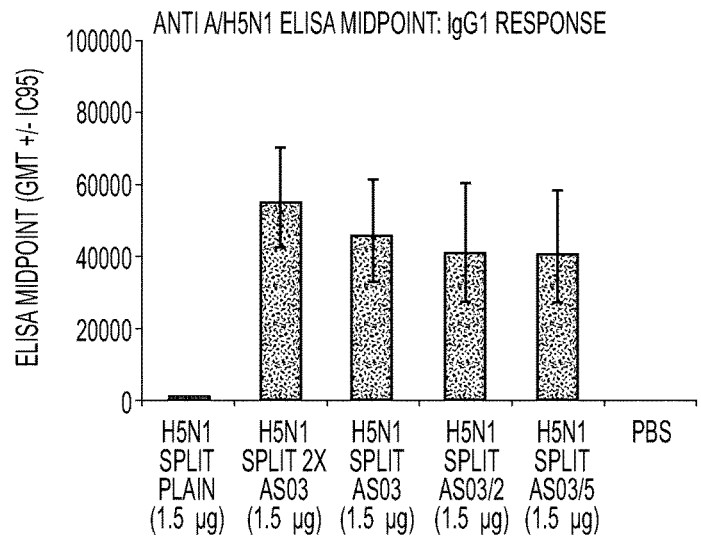
Figure 9D:
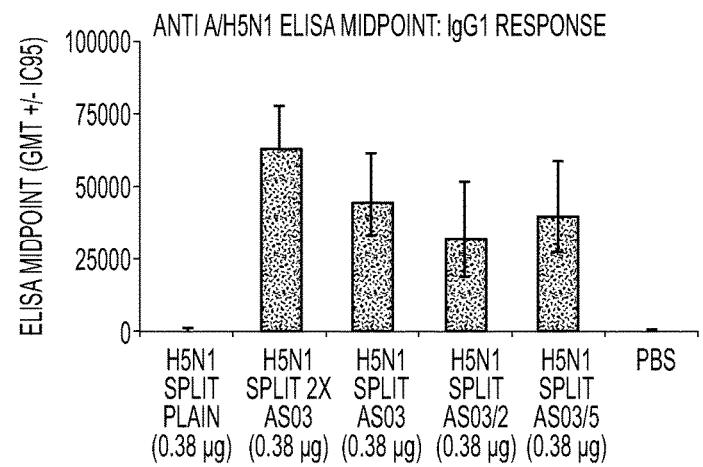
Figure 9E:
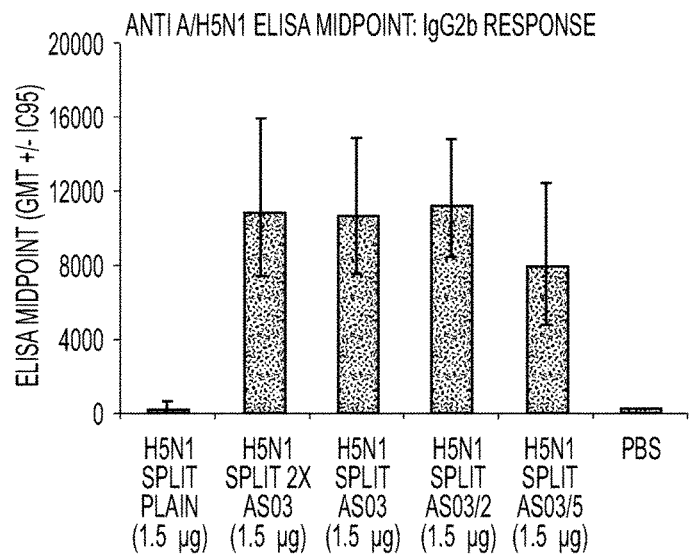
Figure 9F:
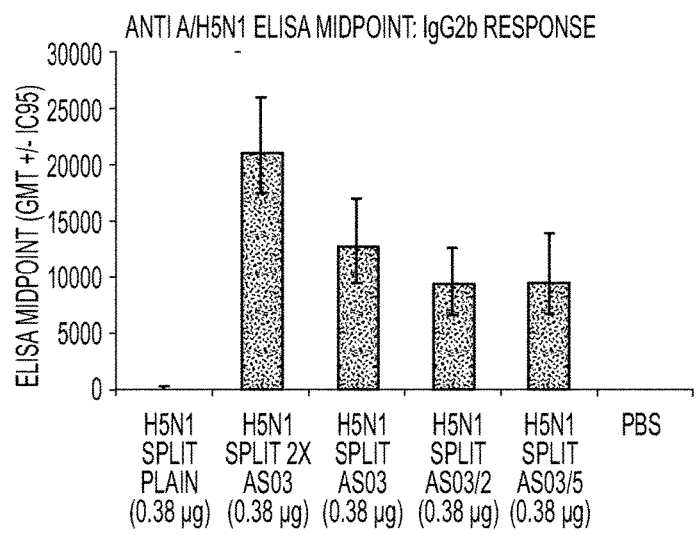
Figure 11A:
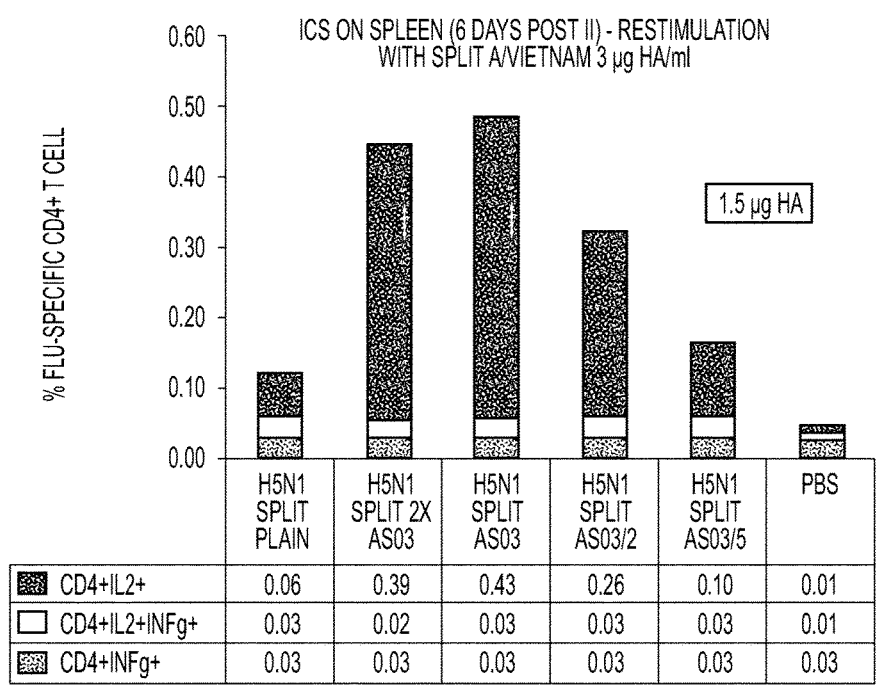
FIGS. 11A-11B: Results of Mice study: Cellular immune response (CD4+ T cell) in naïve C57Bl/6 mice immunized with different dose of H5N1 vaccine (1.5 or 0.38 µg) adjuvanted with dose range AS03: (FIG. A) 1.5 µg HA Ag (antigen) or (FIG. B) 0.38 µg HA Ag (antigen).
Figure 11B:
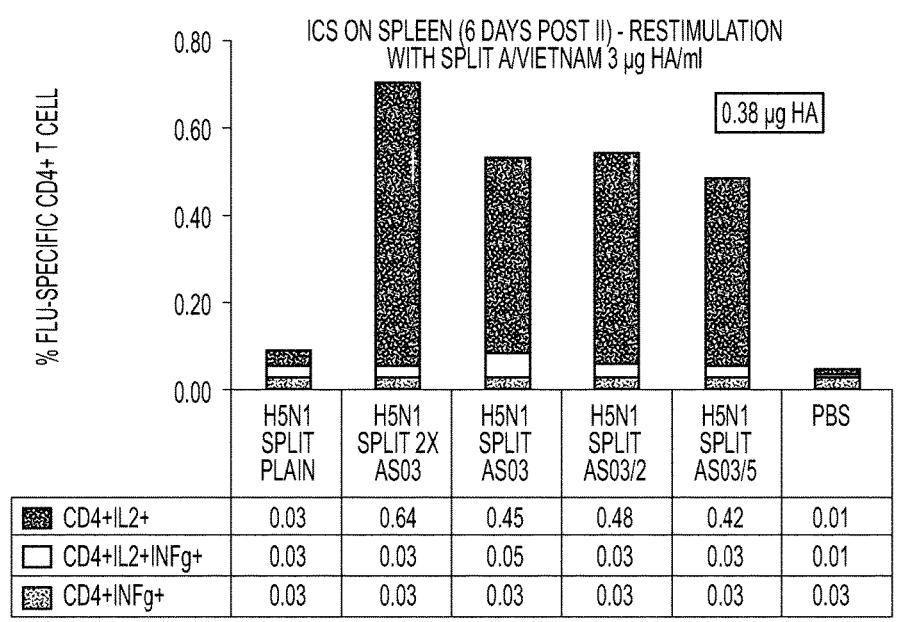

Results are presented in FIG. 5. In this mouse model of heterosubtypic priming followed by single vaccination, AS03 and dilutions thereof were shown to induce higher HI titres compared to the plain vaccine. For all influenza A strains, a statistically significant increase of HI titres was observed ($p<0.05$). For the H1N1 strain, a significant difference in HI titres was also observed between AS03 and AS03 1/5 ($p<0.05$). A reduced dose of AS03 failed to increase HI titres for all three strains compared to the plain vaccine. Very low responses were observed against the B strain (B/Shangdong); this is likely to be due to the significant antigenic drift between the B strains used for the priming and the vaccine.

IV.3. Summary of Results and Conclusions

In conclusion, an increase in HI titres was observed in animals primed with heterosubtypic strains when using AS03 adjuvanted vaccines compared to the plain vaccine. A full dose of AS03 was optimal for obtaining robust HI titres against all three influenza vaccine strains.

Example V—Preclinical Evaluation of Adjuvanted and Non-Adjuvanted Split Influenza Vaccines (Comprising Various Doses of AS03 Adjuvant) in Primed C57Bl/6 Mice V.1. Experimental Design and Objective Experiments in influenza-primed mice were performed in order to evaluate the increase in humoral and cellular responses by AS03 induced influenza vaccines formulated with this oil-in-water adjuvant.

To simulate the human situation, an experiment was conducted using mice primed with heterosubtypic strains.

V.1.1. Treatment/Group (Table 11)

Groups of 25 adult female C57Bl/6 mice were primed intranasally (20 μl volume) on day 0 with trivalent whole, formalin-inactivated influenza virus (5 μg HA for each strain). Priming strains consisted of earlier drift variants (5 μg HA whole inactivated H1N1 A/Beijing/262/95, H3N2 A/Panama/2007/99, B/Shangdong/7/97) to those included in the vaccine. Twenty-eight days later, the mice were vaccinated with a single dose of the vaccine candidate intramuscularly in a total volume of 100 μl. Mice were immunized with formulations containing split antigens alone (trivalent split plain) or formulations containing split antigens adjuvanted with three doses of AS03 (full, ½ or ⅕). The strains used for the immunizations included H1N1 A/New Caledonia/20/99, H3N2 A/New York/55/2004, B/Jiangsu/10/2003 viral antigens (1.5 μg/strain, $1/10^{th}$ of the human dose).

TABLE 11

| Gr | Antigen/Formulation | Other treatment |
|---|---|---|
| 1 | Trivalent split/Plain (non-adjuvanted) | Heterologous priming D0 |
| 2 | Trivalent split/AS03 | Heterologous priming D0 |
| 3 | Trivalent split/AS03 1/2 | Heterologous priming D0 |
| 4 | Trivalent split/AS03 1/5 | Heterologous priming D0 |
| 5 | PBS | Heterologous priming D0 |

V.1.2. Preparation of the Vaccine Formulations

Trivalent Split/Plain

The formulations for a 100 μl dose are prepared extemporaneously according the following sequence: Water For Injection+Saline Buffer (10 fold concentrated PBS pH 7.4 prepared as taught in example IV)+FLUARIX™ influenza virus vaccine Clinical Lot DFLUA014 (1.5 μg per strain in the final dose).

Trivalent Split/AS03

The formulations for a 100 μl dose are prepared extemporaneously according the following sequence: Water For Injection+Saline Buffer (10 fold concentrated PBS pH 7.4 prepared as taught in example IV)+FLUARIX™ influenza virus vaccine Clinical Lot DFLUA014 (1.5 μg per strain in the final dose)+25 μl SB62 emulsion for the full dose or 12.5 μl SB 62 emulsion for the ½ dose or 5 μl SB62 emulsion for the ⅕ dose. The formulations are injected within the hour following the end of the preparation.

V.1.3. Read-Outs (Table 12)

The humoral immune response to vaccination was measured 21 days after immunization (10 mice/group) and the serum samples were tested by the haemagglutination inhibition (HI) test. The cellular immune response was tested 7 days post-immunization by intracellular cytokine staining (ICS).

TABLE 12

| Read-out | Timepoint | Sample type | Analysis method |
|---|---|---|---|
| Humoral response | D49 | Sera | IHA |
| Cellular response | D35 | PBMCs | ICS |

V.2. Results

V.2.1. Humoral Immunity (10 Mice/Group).

Results are presented in FIG. 6. In this mouse model of heterosubtypic priming followed by single vaccination, AS03 and dilutions (½ and ⅕) thereof were shown to induce higher HI titres compared to the plain vaccine. For all three strains, no difference of HI titres was observed between mice receiving the vaccine adjuvanted with a full dose AS03 or reduced doses AS03.

V.2.2. Cellular Immunity (15 Mice/Group).

Results are presented in FIG. 7. Whatever the dilution of AS03, higher CD4+ T cell responses were observed in mice immunized with AS03-adjuvanted trivalent split vaccine compared to mice immunized with trivalent split plain. Compared to the response induced in mice immunized with trivalent split adjuvanted with a full dose AS03, a trend for lower cellular responses was observed when mice were immunized with trivalent split adjuvanted with lower doses of AS03.

V.3. Summary of Results and Conclusions

In conclusion, an increase in humoral and cellular responses was observed in animals primed with heterosubtypic strains when using AS03 adjuvanted vaccines compared to the plain vaccine. A similar magnitude of humoral response was observed between mice immunized with full dose or fractional doses of AS03 adjuvant. However, a reduction in adjuvant dose was associated with a trend for reduced magnitude of CD4+ T cell response.

Example VI—Preclinical Evaluation of the Cellular Immune Response Induced by Adjuvanted and Non-Adjuvanted Split Influenza Vaccines (Comprising Various Doses of AS03 Adjuvant and Low Dose Antigen) in Primed C57Bl/6 Mice VI.1. Experimental Design and Objective Experiments in influenza-primed mice were performed in order to evaluate the increase in cellular immune responses by AS03 induced by influenza vaccines containing low dose antigen (0.5 μg/strain, $1/30^{th}$ human dose) and formulated with this oil-in-water adjuvant. To simulate the human situation, an experiment was conducted using mice primed with heterosubtypic strains.

VI.1.1. Treatment/Group (Table 13)

Groups of 15 adult female C57Bl/6 mice were primed intranasally (20 μl volume) on day 0 with trivalent whole, formalin-inactivated influenza virus (5 μg HA for each strain). Priming strains consisted of earlier drift variants (5 μg HA whole inactivated H1N1 A/Beijing/262/95, H3N2 A/Panama/2007/99, B/Shangdong/7/97) to those included in the vaccine. Twenty-eight days later, the mice were vaccinated with a single dose of the vaccine candidate intramuscularly in a total volume of 50 μl. Mice were immunized with formulations containing split antigens alone (trivalent split plain) or formulations containing split antigens adjuvanted with three doses of AS03 (full, ½ or ⅕). The strains used for the immunizations included H1N1 A/New Caledonia/20/99, H3N2 A/New York/55/2004, B/Jiangsu/10/2003 viral antigens (0.5 µg/strain, $\frac{1}{30}^{th}$ of the human dose).

TABLE 13

| Gr | Antigen/Formulation | Other treatment |
|---|---|---|
| 1 | Trivalent split/Plain (non-adjuvanted) | Heterologous priming D0 |
| 2 | Trivalent split/AS03 | Heterologous priming D0 |
| 3 | Trivalent split/AS03 1/2 | Heterologous priming D0 |
| 4 | Trivalent split/AS03 1/5 | Heterologous priming D0 |
| 5 | PBS | Heterologous priming D0 |

VI.1.2. Preparation of the Vaccine Formulations

Trivalent Split/Plain

The formulations for a 50 µl dose are prepared extemporaneously according the following sequence: Water For Injection+Saline Buffer (10 fold concentrated PBS pH 7.4 prepared as taught in example IV)+FLUARIX™ influenza virus vaccine Clinical Lot DFLUA014 (0.5 µg per strain in the final dose).

Trivalent Split/AS03

The formulations for a 50 µl dose are prepared extemporaneously according the following sequence: Water For Injection+Saline Buffer (10 fold concentrated PBS pH 7.4 prepared as taught in example IV)+FLUARIX™ influenza virus vaccine Clinical Lot DFLUA014 (0.5 µg per strain in the final dose)+25 µl SB62 emulsion for the full dose or 12.5 µl SB 62 emulsion for the ½ dose or 5 µl SB62 emulsion for the ⅕ dose. The formulations are injected within the hour following the end of the preparation.

VI.1.3. Read-Outs (Table 14)

The cellular immune response was tested 7 days post-immunization by intracellular cytokine staining.

TABLE 14

| Read-out | Timepoint | Sample type | Analysis method |
|---|---|---|---|
| Cellular response | D35 | PBMCs | ICS |

VI.2. Results

VI.2.1. Cellular Immunity

Results are presented in FIG. 8. Marginally higher CD4+ T cell responses were observed in mice immunized with trivalent split vaccine adjuvanted with AS03 (full or ½ dose) compared to mice immunized with trivalent split plain. Compared to the response induced in mice immunized with trivalent split plain or adjuvanted with a full dose or a half dose of AS03, higher cellular responses were observed when mice were immunized with trivalent split adjuvanted with 1/5 of AS03 dose.

VI.3. Summary of Results and Conclusions

In conclusion, a minimal increase in CD4+ T cell responses was observed in heterosubtypic primed animals when using AS03 adjuvanted vaccines compared to the plain vaccine. No adjuvant dose response was observed in this experiment and indeed a ⅕ of AS03 dose induced higher frequencies of antigen specific CD4+ T cells than was seen with higher adjuvant doses. Overall these data are not consistent with other preclinical experiments and may be suggestive of a technical issue with this particular experiment.

Example VII—Preclinical Evaluation of Adjuvanted and Non-Adjuvanted Split H5N1 Vaccines (Comprising Various Doses of AS03 Adjuvant and Antigen) in Naïve C57Bl/6 Mice VII.1. Experimental Design and Objective Experiments in H5N1-naive mice were performed in order to evaluate the increase in humoral and cellular immune responses by AS03 induced by H5N1 split vaccines formulated with this oil-in-water adjuvant. In the case of a pandemic, it is expected that the entire world population will be immunologically naive to the newly circulating pandemic influenza strain. Due to this naive immune status a pandemic vaccine will likely require two vaccine doses to protect individuals from infection and severe illness caused by a new influenza strain. To represent this lack of previous exposure a naïve mouse model was developed to assess vaccine immunogenicity.

V11.1.1. Treatment/Group (Table 15)

Groups of 15 adult female naïve C57Bl/6 mice were immunized on days 0 and 28 with pandemic H5N1 vaccine candidate intramuscularly in a total volume of 50 µl. Mice were immunized with formulations containing split H5N1 antigens alone (H5N1 split plain) or formulations containing split antigens adjuvanted with different doses of AS03 (double, full, ½ or ⅕). The strains used for the immunizations included H5N1 A/Vietnam/1194/04 viral antigen (1.5 or 0.38 µg/strain corresponding to $\frac{1}{10}^{th}$ of the human dose). No formulation was done with a double AS03 dose but rather a concomitant injection of one 50 µl H5N1 split/AS03 full dose+one 50 µl dose AS03.

TABLE 15

| Gr | Antigen/Formulation | Antigen dose |
|---|---|---|
| 1 | H5N1 split/Plain (non-adjuvanted) | 1.5 µg |
| 2 | H5N1 split/double dose AS03 | 1.5 µg |
| 3 | H5N1 split/AS03 | 1.5 µg |
| 4 | H5N1 split/AS03 1/2 | 1.5 µg |
| 5 | H5N1 split/AS03 1/5 | 1.5 µg |
| 6 | H5N1 split/Plain (non-adjuvanted) | 0.38 µg |
| 7 | H5N1 split/double dose AS03 | 0.38 µg |
| 8 | H5N1 split/AS03 | 0.38 µg |
| 9 | H5N1 split/AS03 1/2 | 0.38 µg |
| 10 | H5N1 split/AS03 1/5 | 0.38 µg |
| 11 | PBS | |

VII.1.2. Preparation of the Vaccine Formulations

Preparation of one liter of Final Bulk Buffer (PBS pH 7.2±0.2): to 0.800 l of water for injection, add NaCl 7.699 g, KCl 0.200 g, $MgCl_2 \times 6H_2O$ 0.100 g, $Na_2HPO_4 \times 12$ $H_2O$ 2.600 g, $KH_2PO_4$ 0.373 g. After solubilization, adjust to 1.0 L with water for injection H5N1 Split/Plain Preparation of a 50 µl Dose:

Thiomersal (quantities taking into account its concentration in the strain) and Triton X100 are added to the Final Bulk Buffer. Tween 80 is not added as the content target in the formulation is reach by the Tween concentration of the strain. The final concentrations are of 10 µg/ml for Thiomersal, 368 µg/ml for Tween 80 and 35 µg/ml for Triton X100 in the 1.5 µg formulation dose. They are of 10 µg/ml for Thiomersal, 93 µg/ml for Tween80 and 8.9 µg/ml for Triton X100 in the 0.38 µg formulation dose. After 5-30 min magnetic stirring 1.5 or 0.38 µg of HA (H5N1 strain) are added. The formulations are stirred for 30-60 minutes. The pH is checked. Injections occur within the hour following the end of the formulation.

H5N1 Split/AS03

Preparation of a 50 µl Dose:

Thiomersal (quantities taking into account its concentration in the strain) and Triton X100 are added to the Final Bulk Buffer. Tween 80 is not added as the content target in the formulation is reach by the Tween concentration of the strain. The final concentrations are of 10 µg/ml for Thiomersal, 368 µg/ml for Tween 80 and 35 µg/ml for Triton X100 in the 1.5 µg formulation dose. They are of 10 µg/ml for Thiomersal, 93 µg/ml for Tween80 and 8.9 µg/ml for Triton X100 in the 0.38 µg formulation dose. After 5-30 min magnetic stirring 1.5 or 0.38 µg of HA (H5N1 strain) are added. After 30-60 minutes magnetic stirring, 25 or 12.5 or 5 µl of SB62 emulsion is added. The formulations are stirred for 30-60 minutes. The pH is checked. Injections occur within the hour following the end of the formulation VII.1.3. Read-Outs (Table 16)

The humoral immune response was measured 14 days after immunization (10 mice/group) by anti-Ig, IgG1 and IgG2b antibody titers (FIG. 9, A-F). The humoral immune response was also measured 21 days after immunization (10 mice/group) by anti-H5N1 hemagglutination inhibition assay (FIG. 10, A-B).

The cellular immune response was tested 6 days post-immunization (5 pools of 3 mice per group) by intracellular cytokine staining (ICS) of antigen-specific CD4+ T cells numerated by flow cytometry (FIG. 11, A-B).

TABLE 16

| Read-out | Timepoint | Sample type | Analysis method |
|---|---|---|---|
| Humoral response | D39 | Sera | ELISA, isotypes and HI titers |
| Cellular response | D34 | PBMCs | ICS |

VII.2. Results

VII.2.1. Humoral immune Response: ELISA and Isotypes.

Results are presented in FIG. 9.

At each dose of H5N1 split vaccine, all adjuvanted groups induced higher anti-H5N1 Ig, IgG1 and IgG2b antibody titers compared to the non-adjuvanted H5N1 split vaccine (FIGS. 9-A to F).

At each dose of H5N1 split vaccine; the anti-H5N1 IgG1 antibody response was 4-5-fold higher than the anti-H5N1 IgG2b antibody response (FIGS. 9-C to F). With a dose of 1.5 μg HA of H5N1 split vaccine and combined with each dose of adjuvant, no difference of anti-H5N1 Ig, IgG1 and IgG2b antibody responses were observed (FIGS. 9-A, C and E).

With a dose of 0.38 μg HA of H5N1 split vaccine, a trend for higher anti-H5N1 Ig titers were obtained after immunization with H5N1 split vaccine adjuvanted with 2×-full dose compared to the response induced by H5N1 split vaccine adjuvanted with AS03/2 (p=0.7315) and AS03 1/5 (p=0.9744) (FIG. 9-B). This trend was also observed for the anti-H5N1 IgG1 antibody response (FIG. 9-D). However, the power was not sufficient to observe a statistically significant difference (25% power for 1.7 fold difference, or 47% for a 2 fold difference).

VII.2.2. Humoral Immune Response: HI Titers.

With a Dose of 1.5 μg HA/Mice:

At each adjuvant dose, all mice immunized with AS03-adjuvanted H5N1 split vaccine induced higher HI titers compared to the response obtained in mice immunized with the non-adjuvanted H5N1 split vaccine (FIG. 10-A). No difference of HI titers were observed when H5N1 split vaccine was adjuvanted with a dose range of AS03 (FIG. 10-A).

With a Dose of 0.38 μg HA/Dose

At each adjuvant dose, all mice immunized with AS03-adjuvanted H5N1 split vaccine induced higher HI titers compared to the response obtained in mice immunized with the non-adjuvanted H5N1 split vaccine (FIG. 10B).

Significantly higher HI titers were observed with H5N1 split vaccine adjuvanted with 2× full dose AS03 compared to the response obtained with H5N1 split vaccine adjuvanted with AS03/2 (p=0.032 for a 4-fold difference) (FIG. 10B).

No difference of HI titers was observed in mice immunized with H5N1 split vaccine adjuvanted with 2× full dose AS03 or a full dose AS03 or between mice immunized with H5N1 split vaccine adjuvanted with AS03/2 or AS03/5 (FIG. 10B).

Comparison Between Antigen Doses (1.5 μg or 0.38 μg):

No difference of HI titers were observed between mice immunized with each HA dose of H5N1 split vaccine adjuvanted with AS03, AS03/2 or AS03/5, except between mice immunized with 1.5 μg HA split H5N1 adjuvanted with AS03/5 and mice immunized with 0.38 μg HA split H5N1 adjuvanted with 2× full dose AS03 (FIG. 10). HI titers were significantly higher following immunization with 0.38 μg HA split H5N1 adjuvanted with 2× full dose AS03 compared to the higher antigen dose combined with lower adjuvant dose (1.5 μg HA with AS03/5, p=0.0193 for a 4-fold difference) (FIG. 10).

VII.2.3. Cellular Immune Response

Results are presented in FIG. 11.

At each dose of H5N1 split vaccine (1.5 or 0.38 μg) higher CD4+ T cell responses were observed in mice immunized with H5N1 split vaccine adjuvanted with various doses of AS03 compared to mice immunized with the non-adjuvanted H5N1 split vaccine (FIG. 11).

At a dose of 1.5 μg H5N1 split vaccine, a reduction of the AS03 doses corresponded to a decrease in CD4+ T cell frequencies (FIG. 11A). However, at a dose of 0.38 μg H5N1 split vaccine no difference in CD4+ T cell responses was observed between different adjuvant doses in mice immunized with AS03-adjuvanted H5N1 split vaccines (FIG. 11B).

VII.3. Summary of Results and Conclusions

Immunogenicity studies in mice showed that adjuvanted H5N1 split vaccine induced significantly higher humoral (anti-H5N1 ELISA and HI titers) and cellular (CD4+ T cells) responses than those induced by the non-adjuvanted H5N1 split vaccine.

No antigen dose response effect was observed for the humoral immune response between mice immunized with 1.5 μg and 0.38 μg adjuvanted H5N1 split vaccine suggesting that in the presence of adjuvant even lower doses of HA may be required to observe a dose response effect in this model.

A strong increase in CD4+ T cell responses was observed in naïve mice when using AS03 adjuvanted H5N1 pandemic vaccines compared to the plain H5N1 vaccine. No impact of the AS03 dilution was observed when a dose of 0.38 μg of H5N1 split vaccine was used as vaccine candidate, while a decrease of CD4 T cell responses was observed when 1.5 μg H5N1 split vaccine was adjuvanted with the reduced dose AS03.

As previously observed, no difference in humoral and cellular immune responses were observed between mice immunized with H5N1 split vaccine (at either antigen dose) adjuvanted with a full dose AS03 or with AS03/2. Some enhancement in the immune response was detected when 2× full dose AS03 was used in the vaccine formulation and accordingly a decrease in the immune response was detected when AS03/5 was used in the vaccine formulation.

Overall, the data reported here support the potency of this novel adjuvant system in this vaccine formulation.

Example VIII—Preclinical Evaluation of Adjuvanted and Non-Adjuvanted Influenza Vaccines in Primed Large White Pigs VIII.1. Experimental Design and Objective Experiment in influenza-primed pigs was performed in order to evaluate the increase in humoral responses by AS03 induced influenza vaccines formulated with this oil-in-water adjuvant.

Pigs were used in order to evaluate a dose range of AS03 in an animal model close to humans. Pigs show a long list of biological analogies that establish this animal as physiologically the closest to man with very few exceptions (Douglas R., 1972). Moreover, the manifestation of influenza infection in pigs is commonly observed.

VIII.1.1. Treatment/Group (Table 17)

Groups of 10 adult Large White female pigs were primed on day 0 with trivalent whole, formalin-inactivated influenza virus (25 µg HA for each strain) intranasally in a total volume of 200 µl. Priming strains consisted of strains homologous to vaccine strains (25 µg HA whole inactivated H1N1 A/New Caledonia/20/99, H3N2 A/Panama/2007/99 and B/Shangdong/7/97). Twenty-eight days later, pigs were vaccinated with a single dose of the vaccine candidate intramuscularly in a total volume of 500 µl. Pigs were immunized with formulations containing split antigens alone (trivalent split plain) or formulations containing split antigens adjuvanted with a dose range of AS03 (full, ½ or ⅕). The strains used for the immunizations included H1N1 A/New Caledonia/20/99, H3N2 A/Panama/2007/99 and B/Shangdong/7/97 viral antigens (15 µg HA for H1N1 A/New Caledonia/20/99, H3N2 A/Panama/2007/99 strains and 17.5 µg B/Shangdong/7/97 strain as in one human dose).

Groups (10 Pigs/Group):

TABLE 17

| Gr | Antigen/Formulation | Other treatment |
|---|---|---|
| 1 | Trivalent split/Plain (non-adjuvanted) | Heterologous priming D0 |
| 2 | Trivalent split/AS03 | Heterologous priming D0 |
| 3 | Trivalent split/AS03 1/2 | Heterologous priming D0 |
| 4 | Trivalent split/AS03 1/5 | Heterologous priming D0 |

VI11.1.2. Preparation of the Vaccine Formulations

Trivalent Split/Plain

A Premix of Tween 80, Triton X100 and Vitamin E Succinate (VES) is prepared in order to reach a final concentration into the vaccine of 750 µg/ml of Tween 80, 110 µg/ml of Triton X100 and 100 µg/ml of VES. The quantities used in the premix take into account their content into the strains.

The formulation of one 500 µl dose is prepared extemporaneously according the following sequence: Water For Injection+Saline Buffer (10 fold concentrated PBS pH 7.4 prepared as taught in example IV)+Premix, 5 min magnetic stirring at room temperature, +15 µg HA H1N1 strain, 10 min magnetic stirring at room temperature, +15 µg HA H3N2 strain, 10 min magnetic stirring at room temperature, +17.5 µg HA B strain, 15 min magnetic stirring at room temperature. The formulations are injected within the hour following the end of their preparation.

Trivalent Split/AS03

A Premix of Tween 80, Triton X100 and Vitamin E Succinate (VES) is prepared in order to reach a final concentration into the vaccine of 750 µg/ml of Tween 80, 110 µg/ml of Triton X100 and 100 µg/ml of VES. The quantities used in the premix take into account their content into the strains.

The formulation of one 500 µl dose is prepared extemporaneously according the following sequence: Water For Injection+Saline Buffer (10 fold concentrated PBS pH 7.4 prepared as taught in example IV)+Premix, 5 min magnetic stirring at room temperature, +15 µg HA H1N1 strain, 10 min magnetic stirring at room temperature, +15 µg HA H3N2 strain, 10 min magnetic stirring at room temperature, +17.5 µg HA B strain, 15 min magnetic stirring at room temperature, +250 µl SB62 emulsion for the full dose AS03 or 125 µl SB62 emulsion for the 1/2 dose AS03 or 50 µl SB62 emulsion for the ⅕ dose AS03, 15 min magnetic stirring at room temperature. The formulations are injected within the hour following the end of their preparation.

VI11.1.3. Read-Outs (Table 18)

The humoral immune response to vaccination was measured before intranasal priming (day 0), before immunization (day 28) and 14 days after immunization (10 pigs/group). Serum samples were tested by the haemagglutination inhibition (HI) test.

TABLE 18

| Read-out | Timepoint | Sample type | Analysis method |
|---|---|---|---|
| Humoral response | D0, D28, D42 | Sera | IHA |

VIII.2. Results and Conclusions

VIII.2.1. Humoral Immunity

Results are presented in FIG. 12. Whatever the dilution of the adjuvant, AS03 adjuvanted trivalent split formulations induced a stronger HI response to all strains than the plain trivalent formulation in this model of homologous priming, although statistical significance was not always reached for all three strains. An adjuvant dose effect was observed with slight differences from strain to strain. For less immunogenic strains such as B/Shangdong, only the trivalent split vaccine adjuvanted with a full dose of AS03 was significantly different from the plain vaccine. In contrast to trivalent split vaccine adjuvanted with a full dose of AS03, a reduced dose of AS03 failed to increase HI titres for all three strains above those seen with the plain vaccine.

The invention claimed is:

1. A method of inducing an immunoprotective response in an adult human patient suffering from or susceptible to an influenza virus infection, comprising administering to the adult human patient an immunogenic composition comprising at least 5 ug of influenza virus hemagglutinin and an adjuvant composition comprising an oil in water emulsion, wherein said oil in water emulsion comprises 5.35 mg squalene, 5.94 mg alpha-tocopherol and 2.425 mg polyoxyethylene sorbitan monooleate, per dose;
    wherein said immunogenic composition elicits an immunoprotective response against influenza virus.

2. The method of claim 1, wherein the immunogenic composition volume is between 0.4 and 1.5 ml per dose.

3. The method of claim 1, wherein said dose volume is 0.5 ml.

4. The method of claim 1, wherein said dose volume is 0.7 ml.

5. The method of claim 1, wherein said dose volume is 1.0 ml.

* * * * *